United States Patent
Franceschi et al.

(10) Patent No.: US 11,553,963 B2
(45) Date of Patent: Jan. 17, 2023

(54) PHRENIC NERVE STIMULATION

(71) Applicant: CIRCLE SAFE, Aubagne (FR)

(72) Inventors: Frédéric Franceschi, Aubagne (FR);
Bertrand Thiery, Aubagne (FR)

(73) Assignee: CIRCLE SAFE, Aubagne (FR)

(*) Notice: Subject to any disclaimer, the term of this patent is extended or adjusted under 35 U.S.C. 154(b) by 0 days.

(21) Appl. No.: 17/689,712

(22) Filed: Mar. 8, 2022

(65) Prior Publication Data
US 2022/0287768 A1 Sep. 15, 2022

(30) Foreign Application Priority Data

Mar. 9, 2021 (EP) .................................... 21305287

(51) Int. Cl.
*A61B 18/14* (2006.01)
*A61B 18/02* (2006.01)
*A61B 18/00* (2006.01)

(52) U.S. Cl.
CPC .......... *A61B 18/1492* (2013.01); *A61B 18/02* (2013.01); *A61B 2018/0022* (2013.01);
(Continued)

(58) Field of Classification Search
CPC ..... A61B 5/746; A61B 5/0538; A61B 5/6852; A61B 5/4893; A61B 5/4041; A61B 18/02; A61B 18/1492
See application file for complete search history.

(56) References Cited

U.S. PATENT DOCUMENTS

| 4,574,807 A | 3/1986 | Hewson et al. |
| 4,683,890 A | 8/1987 | Hewson |

(Continued)

FOREIGN PATENT DOCUMENTS

| EP | 0010908 B1 | 4/1983 |
| EP | 0311927 A1 | 4/1989 |

(Continued)

OTHER PUBLICATIONS

Anwar, O. et al., "Contemporary analysis of phrenic nerve injuries following cryoballoon-based pulmonary vein isolation: A single-centre experience with the systematic use of compound motor action potential monitoring," PLoS One, vol. 15, No. 6, Jun. 25, 2020, 11 pages.

(Continued)

*Primary Examiner* — Ronald Hupczey, Jr.
(74) *Attorney, Agent, or Firm* — Alleman Hall Creasman & Tuttle LLP

(57) ABSTRACT

The disclosure notably relates to a system for phrenic nerve stimulation. The stimulation system comprises a catheter including one or more intravascular electrodes each arranged on a distal portion of the catheter. The catheter is configured to be introduced in the superior vena cava of a human patient. The stimulation system also comprises an extracorporeal electrode patch configured to be affixed to the patient opposite to the distal portion relative to the phrenic nerve. The extracorporeal electrode patch is operable in a bipolar mode with the one or more intravascular electrodes. Such a system forms an improved solution for phrenic nerve stimulation, in particular during a cryoablation procedure.

9 Claims, 6 Drawing Sheets

(52) U.S. Cl.
CPC .............. *A61B 2018/00351* (2013.01); *A61B 2018/00577* (2013.01); *A61B 2018/0212* (2013.01)

(56) References Cited

U.S. PATENT DOCUMENTS

| | | |
|---|---|---|
| 5,052,390 A | 10/1991 | Hewson |
| 8,412,350 B2 | 4/2013 | Bly |
| 8,456,182 B2 | 6/2013 | Bar-Tal et al. |
| 8,897,879 B2 | 11/2014 | Karamanoglu et al. |
| 9,050,453 B2 | 6/2015 | Inagaki et al. |
| 9,168,377 B2 | 10/2015 | Hoffer |
| 9,333,363 B2 | 5/2016 | Hoffer et al. |
| 9,415,225 B2 | 8/2016 | Shuros et al. |
| 10,064,564 B2 | 9/2018 | Kowalski et al. |
| 10,507,322 B2 | 12/2019 | Westlund et al. |
| 10,512,772 B2 | 12/2019 | Hoffer et al. |
| 2002/0165532 A1 | 11/2002 | Hill, III et al. |
| 2006/0282124 A1 | 12/2006 | Diaz et al. |
| 2008/0009846 A1* | 1/2008 | Ward .................... A61B 18/16 606/32 |
| 2008/0281312 A1* | 11/2008 | Werneth ............. A61B 18/1206 128/898 |
| 2010/0079158 A1 | 4/2010 | Bar-Tal et al. |
| 2013/0030496 A1 | 1/2013 | Karamanoglu et al. |
| 2013/0296840 A1* | 11/2013 | Condie .................. A61B 90/06 606/33 |
| 2015/0057563 A1 | 2/2015 | Kowalski et al. |
| 2015/0141798 A1 | 5/2015 | Bar-Tal |
| 2015/0265833 A1 | 9/2015 | Meyyappan et al. |
| 2016/0220822 A1* | 8/2016 | Hoffer .................. A61B 5/6852 |
| 2017/0189106 A1* | 7/2017 | Schuler .................... A61B 5/00 |
| 2018/0344244 A1 | 12/2018 | Botzer et al. |
| 2020/0077938 A1 | 3/2020 | Jung et al. |

FOREIGN PATENT DOCUMENTS

| | | | |
|---|---|---|---|
| EP | 1572293 | 9/2005 | |
| EP | 1802370 B1 | 1/2011 | |
| EP | 2371416 A1 | 10/2011 | |
| WO | WO-2018212840 A1 * | 11/2018 | ............. A61B 18/02 |

OTHER PUBLICATIONS

Arai, T. et al., "A new method of superior vena cava isolation without phrenic nerve injury by longitudinal ablation parallel to the phrenic nerve: a case report," European Heart Journal—Case Reports, vol. 4, No. 5, Sep. 9, 2020, 4 pages.

Augostini, R. et al., "How to implant a phrenic nerve stimulator for treatment of central sleep apnea?" Journal of Cardiovascular Electrophysiology, vol. 30, No. 5, Mar. 4, 2019, 8 pages.

Dimarco, A. et al., "Combined Intercostal and Diaphragm Pacing to Provide Artificial Ventilation in Patients With Tetraplegia," Archives of Physical Medicine and Rehabilitation, vol. 86, No. 6, Jun. 2005, 8 pages.

European Patent Office, Extended European Search Report Issued in Application No. 21305287.1, dated Sep. 6, 2021, Germany, 7 pages.

Kaczmarek, K. et al., "Straight and crosier-shaped catheter techniques for phrenic nerve stimulation during cryoballoon pulmonary vein isolation for the treatment of atrial fibrillation," Kardiologia Polska, vol. 77, No. 9, Jul. 22, 2019, 7 pages.

Chikata, A. et al., "Coronary sinus catheter placement via left cubital vein for phrenic nerve stimulation during pulmonary vein isolation," Heart and Vessels, vol. 34, Apr. 10, 2019, 7 pages.

Reynolds, S. et al., "Diaphragm Activation in Ventilated Patients Using a Novel Transvenous Phrenic Nerve Pacing Catheter," Critical Care Medicine, vol. 45, No. 7, Jul. 1, 2017, 4 pages.

* cited by examiner

PHRENIC NERVE STIMULATION

TECHNICAL FIELD

The present disclosure relates to systems, methods, a kit, and a computer program, for phrenic nerve stimulation and/or cardiac cryoablation.

BACKGROUND

Atrial fibrillation is a common arrhythmia. One of the treatments offered is ablation of atrial fibrillation with a minimally invasive procedure. Atrial fibrillation ablation is a type of cardiac ablation, which works by scarring or destroying tissue in the heart to disrupt faulty electrical signals causing the arrhythmia. For example, one or both pulmonary veins may be isolated by creating a circumferential lesion, e.g., surrounding their ostia. Among minimally invasive cardiac ablation techniques, cardiac cryoablation is a procedure gaining popularity among electrophysiology practitioners. Cryoablation techniques consist in electrical isolation of the pulmonary veins of the heart by cold "burning" of the tissues with a cryoablation catheter, most often a cryoballoon catheter (i.e., cryogenic balloon catheter).

The most common complication of cryoablation techniques is right diaphragmatic palsy caused by injury of the right phrenic nerve, due to the close proximity between the right phrenic nerve and the pulmonary veins. Although such injury does not systematically occur during cryoablation procedures, it still affects a non-negligible number of patients. And even though the injury is most often reversible, a relatively significant part of the concerned patients is still affected on the next day, and for some patients the diaphragmatic palsy may last over a relatively long period of time before self-cure.

The research article "*Contemporary analysis of phrenic nerve injuries following cryoballoon-based pulmonary vein isolation: A single-centre experience with the systematic use of compound motor action potential monitoring*", Anwar, O. et. al., 2020, provides an overview of injury of the right phrenic nerve due to cryoablation, as well as techniques for reducing such injury and issues related to such techniques. One technique widely spread and reviewed in this paper is to perform an electric stimulation of the right phrenic nerve during the cryoablation procedure. As the phrenic nerve controls muscle contraction of the right diaphragmatic dome, the technique further comprises monitoring the contraction response induced by the electrical stimulation and act thereupon.

FIG. 1 illustrates the conventional manner in the prior art to perform such a phrenic nerve stimulation technique. The figure shows an example of an anatomical section H of the heart on the left side and a corresponding medical image I on the right side, exemplifying the positioning of an electrophysiology catheter 10 for electrical stimulation of the right phrenic nerve PN. Stimulation catheter 10 is introduced through the femoral vein and positioned with its distal end 14 inside the superior vena cava VC to stimulate the phrenic nerve PN. Stimulation catheter 10 comprises at its distal end 14 several (e.g., four) electrodes 11 which are positioned inside the superior vena cava (above the heart), to be as close as possible and facing the phrenic nerve PN. Stimulation catheter 10 may be a straight quadripolar catheter, a commercially available catheter commonly used. The operator places the electrodes 11 to stimulate the phrenic nerve by operating in a bipolar mode two electrodes. The operator observes the right diaphragmatic contraction caused by the electrical stimulation, which helps the operator to make assessments on possible injury of the right phrenic nerve. Such assessments allow the operator to make clinical decisions to reduce possibilities of complications.

Such an electrical stimulation presents several issues. First, the operator needs to initially locate the position where the phrenic nerve can be stimulated with the electrodes of the stimulation catheter. If the operator "misses" the position, the current supplied by the electrodes is inefficient to stimulate the phrenic nerve. Therefore, the operator is presented with the inconvenience of having to make sure that the stimulation catheter is well positioned. Moreover, even if the operator has made sure that the stimulation catheter is well positioned prior to applying the electrical stimulation, the operator needs to make sure that the stimulation catheter is maintained at said location while applying the electrical stimulation, so that the electrical stimulation on the phrenic nerve is stable. Maintaining stability of the electrical stimulation is a difficult task for the operator while using currently available stimulation catheters. Thus, the operator may at times "lose" the phrenic nerve while applying the electrical stimulation, and this renders the electrical stimulation unstable. To correct the stimulation, the operator needs to reposition the catheter. This causes inconvenience to the operator who loses time to relocate the stimulation catheter and restart the stimulation. Moreover, the procedure relies on diaphragmatic monitoring to assess the injury of the phrenic nerve. However, if diaphragmatic monitoring becomes unavailable due to instability, the operator is unable to assess injury of the phrenic nerve. In addition, an unstable stimulation may at times yield a reduction in diaphragmatic contraction response falsely interpreted as an injury or an upcoming injury of the phrenic nerve, thereby misleading the operator when the reduction is only due to misplacement of the catheter.

Within this context, there is still a need for an improved solution for phrenic nerve stimulation, in particular during a cryoablation procedure.

SUMMARY

It is therefore provided a system for phrenic nerve stimulation. The stimulation system comprises a (stimulation) catheter including one or more intravascular electrodes each arranged on a distal portion of the catheter. The catheter is configured to be introduced in the superior vena cava of a human patient so as to position the distal portion in the superior vena cava, in the right brachiocephalic vein, and/or in the right subclavian vein. The stimulation system also comprises an extracorporeal electrode patch configured to be affixed to the patient opposite to the distal portion relative to the phrenic nerve. The extracorporeal electrode patch is operable in a bipolar mode with the one or more intravascular electrodes.

In examples, the extracorporeal electrode patch may comprise a conductive surface presenting a length higher than 1 cm and/or a width higher than 1 cm. For example, the conductive surface may present a length higher than 4 cm and a width higher than 2 cm, such as a length higher than 8 cm and a width higher than 4 cm. Optionally, the length of the conductive surface may be smaller than 40 cm or 30 cm, and/or the width of the conductive surface may be smaller than 30 cm or 20 cm. For example, the conductive surface may present a length smaller than 30 cm and a width smaller than 20 cm. For instance, the conductive surface may present a length of about 20 cm and a width of about 10 cm.

In examples, the extracorporeal electrode patch may comprise a conductive layer made of a flexible and/or metallic material. For example, the extracorporeal electrode may be made of a flexible metallic layer. Additionally or alternatively, the extracorporeal electrode patch may comprise a conductive adhesive coating.

In examples, the distal portion of the stimulation catheter may comprise an expandable portion and the stimulation catheter may have an expanded configuration.

In such examples, the expandable portion may be configured to circumferentially fit the inner wall of the superior vena cava, of the right brachiocephalic vein, and/or of the right subclavian vein, preferably so as to remain in position during phrenic nerve stimulation. Additionally or alternatively, the one or more intravascular electrodes may be arranged at least partly on the expandable portion. In such a case, optionally, at least one intravascular electrode arranged on the expandable portion may present a length higher than a width and may be arranged on the expandable portion so as to extend substantially along the superior vena cava, the right brachiocephalic vein, and/or the right subclavian vein when the stimulation catheter is in the expanded configuration. Yet additionally or alternatively, at least one intravascular electrode may be arranged on the expandable portion so as to be in contact with an inner wall of the superior vena cava, of the right brachiocephalic vein, and/or of the right subclavian vein when the stimulation catheter is in the expanded configuration.

Additionally or alternatively in such examples, in the expanded configuration, the one or more intravascular electrodes may be positioned circumferentially on the expandable portion.

Additionally or alternatively in such examples, the expanded configuration may be a helical configuration or spiral configuration, a loop configuration, a lasso configuration, an umbrella configuration, or a basket configuration.

Additionally or alternatively in such examples, the expandable portion may form a helix or spiral having at most two coils in the expanded configuration.

Additionally or alternatively in such examples, the catheter may comprise a non-expandable distal end after the expandable portion.

Additionally or alternatively in such examples, the non-expandable distal end may be straight.

Additionally or alternatively in such examples, the non-expandable distal end may have a length higher than 1 cm, and/or lower than 12 cm, for example between 1.5 cm and 4 cm.

Additionally or alternatively in such examples, the expandable portion may have a diameter between 10 mm and 35 mm in the expanded configuration.

Additionally or alternatively in such examples, the stimulation catheter may comprise one or more pull-wires actionable for deforming the stimulation catheter into the expanded configuration, and/or the expandable portion may be at least partially made of a shape memory material biasing the expandable portion into the expanded configuration.

In examples, the catheter may comprise a lumen for introducing a retractable inner straightening member.

In such examples, the catheter may further comprise the inner straightening member inside the lumen.

Additionally or alternatively in such examples, the inner straightening member may be a guidewire.

Additionally or alternatively in such examples, the guidewire may be metallic, may present a diameter above 0.020" and/or below 0.060", preferably above above 0.030" and/or below 0.040", for example equal to 0.032" or to 0.035", and/or may be made of a hydrophobic material.

In examples, the one or more intravascular electrodes may comprise several electrodes spaced apart along the stimulation catheter. In such examples, optionally, the several electrodes may comprise more than five electrodes and/or less than twenty electrodes. For example, the several electrodes may comprise about ten electrodes. Additionally or alternatively, in such examples, the several electrodes may be spaced apart from a distance above 4 mm and/or below 18 mm, for example about 9 mm. Yet additionally or alternatively, the several electrodes may be connected together so as to form a single pole.

In examples, at least one intravascular electrode may present a length above 0.5 mm and/or below 2.5 cm. Additionally or alternatively, at least one intravascular electrode may present a width above 0.3 mm and/or below 2.5 mm.

In examples, the system further may comprise an energy source configured to be in electrical communication with the one or more intravascular electrodes and with the extracorporeal electrode patch. For example, the energy source may be configured to deliver electric pulses, for instance each of a voltage amplitude between 1V and 50V, and/or each of a duration between 0.1 ms and 20 ms.

In examples, the one or more intravascular electrodes may comprise a plurality of electrodes electrically connected together so as to form a single pole, or a plurality of individual electrodes electrically disconnected one from the other and operable altogether as a single pole.

In examples, the one or more intravascular electrodes may comprise a plurality of electrodes, the system being configured for operating the plurality of electrodes so as to deliver simultaneously an electric pulse between each respective electrode of the plurality of electrodes and the extracorporeal electrode patch.

It is further provided a system for cardiac cryoablation. The cryoablation system comprises the stimulation system, and a cryoablation catheter, for example a cryogenic balloon catheter.

It is further provided a method of phrenic nerve stimulation. The stimulation method comprises providing the system of phrenic nerve stimulation, affixing the extracorporeal electrode patch to a human patient opposite to the distal portion relative to the phrenic nerve, introducing the stimulation catheter in the superior vena cava of the patient, positioning the distal portion of the stimulation catheter in the superior vena cava, in the right brachiocephalic vein, and/or in the right subclavian vein, and operating the extracorporeal electrode patch in a bipolar mode with the one or more intravascular electrodes to perform phrenic nerve stimulation.

By "opposite to the distal portion relative to the phrenic nerve", it is meant any part of the patient's skin which is approximately across the phrenic nerve from the distal portion's location (i.e., superior vena cava, right brachiocephalic vein, and/or right subclavian vein). It is thus meant exactly the region of the patient's upper body consisting of the back (i.e., dorsum), the right side of the upper body (i.e., between the back and the chest, below the right armpit and above the right hip, excluding the right arm and the side of the right shoulder), the top of the right shoulder, and the back of the neck. Thus, the chest, the abdomen, and the right arm (including the side of the right shoulder) do not belong to said region.

In examples, the extracorporeal patch may be affixed at least partly (e.g., fully) on the right half of the patient's back and/or at least partly on the right side of the upper body (excluding the right arm). Additionally or alternatively, the extracorporeal patch may be positioned such that at least part of the extracorporeal patch is at substantially a same height as the distal portion of the stimulation catheter, with respect to the patient's height (i.e., from the feet to the head of the patient). For example, the extracorporeal patch may be affixed below and substantially up to the base of the neck, below and substantially up to the right shoulder, or below and substantially up to the right armpit. Thus, the extracorporeal patch may face the distal portion and/or the one or more intravascular electrodes of the stimulation catheter, that is, a horizontal line may link both. In other words, the extracorporeal patch may be positioned such that the phrenic nerve lies substantially between the extracorporeal patch and the distal portion and/or the one or more intravascular electrodes of the stimulation catheter.

In particular examples, the extracorporeal electrode patch may be affixed at least partly to the back at the right paraspinal, facing the inner part of the right scapula, and the extracorporeal electrode patch may go up to the base of the neck. Additionally or alternatively, the extracorporeal electrode patch may be affixed at least partly to the right latero-thoracic region of the patient.

In examples, the extracorporeal electrode patch may be affixed such that the extracorporeal electrode patch extends along the back or right side of the patient (i.e., longitudinal extension in the direction of the patient from the feet to the head). Alternatively, the extracorporeal electrode patch may be affixed such that the extracorporeal electrode patch extends laterally along the back and the right side of the patient.

In examples, the stimulation method may further comprise positioning at least one electrode against a portion of the inner wall of the superior vena cava, the right brachiocephalic vein, and/or the right subclavian vein, which faces the phrenic nerve.

In examples, the stimulation method may further comprise monitoring a diaphragmatic response to the phrenic nerve stimulation.

It is further provided a method of cryoablation. The cryoablation method comprises introducing a cryoablation catheter inside a left atrium of a human patient, performing cryoablation, and while performing cryoablation, repeating the method of phrenic nerve stimulation, including monitoring a diaphragmatic response to the phrenic nerve stimulation. When the diaphragmatic response decreases, the cryoablation method may further comprise pausing the cryoablation, and resuming the cryoablation afterwards.

It is further provided a kit for phrenic nerve stimulation. The kit comprises the stimulation system or the cryoablation system. The kit also comprises instructions for phrenic nerve stimulation of a human patient, for example during cardiac cryoablation, and optionally instructions for monitoring a diaphragmatic response to phrenic nerve stimulation and/or instructions for performing a cardiac cryoablation.

It is further proposed a computer program comprising executable code for operating the energy source of the stimulation system, for example so as to perform the stimulation method. The computer program may be recorded on non-volatile memory and cause a processor to operate the energy source, for example so as to deliver electric pulses configured for phrenic nerve stimulation. The stimulation system may comprise such a processor and/or such non-volatile memory, for example as part of an energy unit comprising the energy source. The stimulation system may further have the computer program recorded on said memory, or alternatively the computer program may be downloadable from a remote location and the stimulation system may be configured for installing the downloaded computer program thereon.

BRIEF DESCRIPTION OF THE DRAWINGS

Embodiments of the invention will now be described, by way of non-limiting example, and in reference to the accompanying drawings, where.

DETAILED DESCRIPTION

Figure 1:
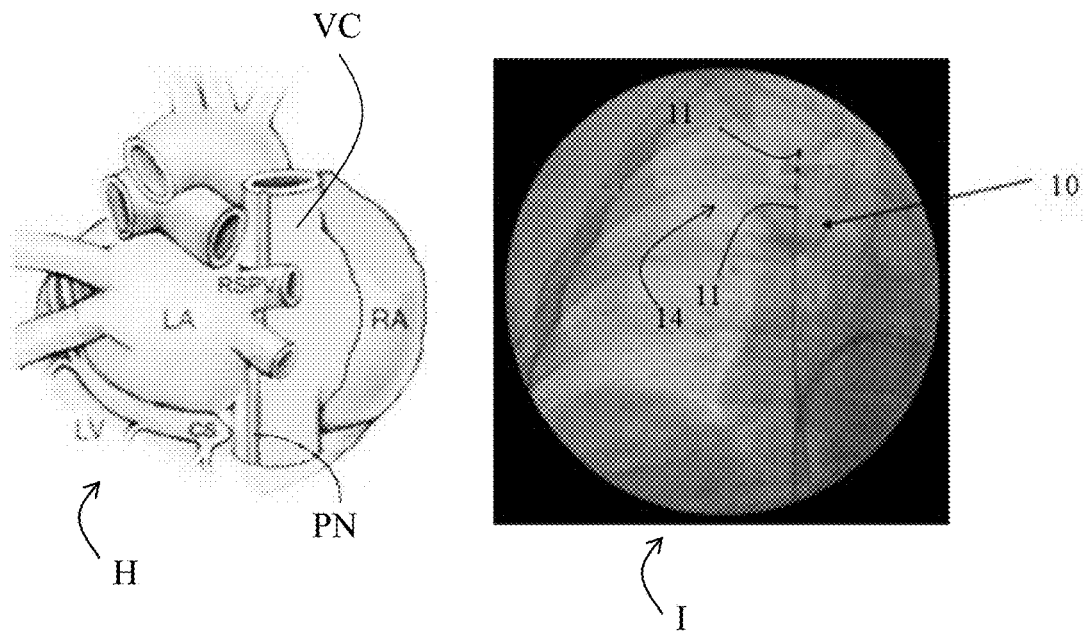
FIG. 1 illustrates a technique of phrenic nerve stimulation according to the prior art.

In the present disclosure, each time it is referred to phrenic nerve stimulation or to "the" phrenic nerve, the right phrenic nerve precisely is meant. Similarly, each time it is referred to diaphragmatic dome contraction or to "the" diaphragm, the right diaphragm precisely is meant. In addition, each time it is referred to the "vena cava" with no further precision, the superior vena cava precisely is meant. Furthermore, each time it is referred to "a patient", a human patient precisely is meant.

In the present disclosure, the following abbreviations are used for physical units: "ms" for milliseconds, "s" for seconds, "mm" for millimeters, "cm" for centimeters, and "V" for Volts, "mV" for millivolts.

The phrenic nerve stimulation system comprises a stimulation catheter and an extracorporeal electrode patch configured to be affixed to a patient. The stimulation catheter is configured to be introduced in the vena cava of the patient so as to position the distal portion in the vena cava, in the right brachiocephalic vein, and/or in the right subclavian vein. The extracorporeal electrode patch is affixed to the patient opposite to the distal portion of the stimulation catheter relative to the phrenic nerve. The stimulation catheter includes one or more intravascular electrodes each arranged on a distal portion of the stimulation catheter. The extracorporeal electrode patch is operable in a bipolar mode with the one or more intravascular electrodes.

Such a stimulation system forms a solution for performing an improved method of phrenic nerve stimulation. The stimulation method comprises providing the stimulation system, affixing the extracorporeal electrode patch to the patient opposite to the distal portion relative to the phrenic nerve, introducing the stimulation catheter in the vena cava of the patient, positioning the distal portion of the stimulation catheter in the vena cava, in the right brachiocephalic vein, and/or in the right subclavian vein, and operating the extracorporeal electrode patch in a bipolar mode with the one or more intravascular electrodes to perform phrenic nerve stimulation.

By "configured to be introduced in the vena cava of the patient so as to position the distal portion in the vena cava, in the right brachiocephalic vein, and/or in the right subclavian vein", it is meant that at least the distal portion of the stimulation catheter is configured to be introduced inside the vena cava, and optionally to be further introduced inside the right brachiocephalic vein, and yet optionally further introduced inside the right subclavian vein. The distal portion of the stimulation catheter may be positioned and operated in the vena cava. Additionally or alternatively, the distal portion of the stimulation catheter may be positioned and operated in both the vena cava and the right brachiocephalic vein, e.g., either selectively or simultaneously in both vessels (with part of the distal portion in one vessel and another part in the other vessel). Additionally or alternatively, the distal portion of the stimulation catheter may be positioned and operated in all of the vena cava, the right brachiocephalic vein and the right subclavian vein, e.g., either selectively or simultaneously in all three vessels and/or pairs (e.g., of consecutive ones) thereof. By "simultaneously", it is meant that the distal portion may be positioned partly in one vessel and partly in another vessel at the same time. Thus, the distal portion of the stimulation catheter may be positioned and operated in any such vessel of the vena cava region near the phrenic nerve. In the following, it is referred to a "vena cava region vessel" to designate such location of the distal portion of the stimulation catheter.

By affixing the extracorporeal electrode patch to the patient opposite to the distal portion relative to the phrenic nerve and operating the stimulation catheter in a bipolar mode with said patch when the stimulation catheter is in a vena cava region vessel of a human patient (i.e., the intravascular electrodes forming altogether one pole and the extracorporeal electrode forming another pole), the stimulation system allows creating an electric field between the one or more intravascular electrodes and the patch that substantially crosses the phrenic nerve. Thus, the electric field stimulates the phrenic nerve so as to yield a contraction response of the diaphragmatic dome.

Thanks to the electric field being created between one or more intravascular electrodes located inside a vena cava region vessel and an extracorporeal electrode located against the patient's back, the stimulation system makes it easier to pass through and thereby stimulate the phrenic nerve. Such a configuration indeed provides that the field is formed between one or more points each near the phrenic nerve (the one or more intravascular electrodes) and another point anatomically on the other side of the phrenic nerve and distant enough, such that there is a tolerance in the positioning of the one or more intravascular electrodes inside the vena cava region vessel, while still reaching the phrenic nerve robustly and stably. As a result, it is easier for the operator to position the one or more intravascular electrodes at the beginning of the procedure. In addition, the stimulation is more stable, in other words, slight movements of the one or more intravascular electrodes do not affect the stimulation, at least not substantially.

Thanks to the extracorporeal electrode being an electrode patch in specific, a relatively large electric field is created, which is thus more likely to cross the phrenic nerve. This allows robustly reaching the phrenic nerve and thereby an even stabler stimulation. In addition, the stimulation system is particularly easy to install. Indeed, an extracorporeal electrode patch is relatively easy to affix to the patient. Besides, the use of a patch allows some tolerance in the positioning of the extracorporeal electrode against the patient, while still reaching the phrenic nerve correctly. Furthermore, during the procedure, the patient may be laying on the back, such that the extracorporeal electrode may be arranged at least partly between the patient and the operating table. The use of a patch helps reducing risks of displacement of the extracorporeal electrode due to movements of the patient's back against the operating table.

The stimulation system may comprise an energy source configured to be in electrical communication with the one or more intravascular electrodes through one pole (for example the anode) and with the extracorporeal electrode patch through another pole (for example the cathode or ground). The energy source is thus configured for creating electrical signals that establish an electrical circuit between the one or more intravascular electrodes and the extracorporeal electrode patch, wherein the electrodes are separated by the resistance of the patient's body. The energy source may comprise an electrophysiology generator adapted for phrenic nerve stimulation.

In examples, the energy source may establish the electrical circuit by delivering electric pulses adapted for phrenic nerve stimulation. Each pulse may have a voltage above 1V and/or below 50V, for example between 2V and 20V, such as about 12V. Additionally or alternatively, each pulse may have a duration above 0.1 ms and/or below 20 ms, for example between 0.5 ms and 10 ms, such as about 2.9 ms. The period between two pairs of consecutive pulses may be constant or variable. In any case, said period may be below 20 s, 10 s or 5 s, and/or above 50 ms or 100 ms, for example between 100 ms and 10s, such as about 1 s. Such period allows securely predicting an upcoming diaphragmatic palsy well-ahead of its occurrence. Indeed, during a cardiac cryoablation procedure, it takes about 30 s between a decrease in diaphragmatic contraction response and the occurrence of the diaphragmatic palsy. The energy source may be configured to repeat delivering such pulses at least for a duration of a cardiac cryoablation procedure, for example at least for a duration of 120 s, such as at least for a duration between 180 s and 240 s. The energy source may be configured to iterate such repetition at least twice in a row (e.g., in less than ten minutes), corresponding to two cardiac cryoablation procedures each on a different right pulmonary vein of a same patient.

By "intravascular electrode", it is meant a unitary conductive portion of the stimulation catheter open to the outside and connectable to a pole. At least one (e.g., each) intravascular electrode of the stimulation catheter may be made of a conductive material, for example metallic, such as gold, platinum, silver, and/or any adequate alloy. The stimulation catheter may comprise one or more electrical leads, the one or more electrical leads being configured for supplying each intravascular electrode in electricity. At least one (e.g., each) electrical lead may be an electrical wire, for example arranged inside the stimulation catheter in one or more lumens, or a conductive path of electrical substrate formed on a surface of the stimulation catheter, for example an inner surface of the stimulation catheter. The stimulation catheter may comprise an electrical connector for (e.g., removably) connecting the catheter to the energy source or to an electrical cord or cable connectable to said energy source, so as to supply each intravascular electrode via the one or more electrical leads.

At least one (e.g., each) intravascular electrode of the stimulation catheter may present the shape of a pad (i.e., isolated block of conductive material delimited by one single curve) formed on an external surface of the stimulation catheter and facing at least part of the walls of the vein. The pad may present any geometry, for example a square shape, a circle shape, or any elongated shape with a length higher than a width, such as a generally rectangular shape, or yet a generally elliptic shape. By "length" respectively "width" of the pad, it is meant the maximal respectively minimal Euclidian distance between a pair of points of the pad when projected on a plane generally parallel to the pad. Additionally or alternatively, instead of a pad, at least one (e.g., each) intravascular electrode may present a ring shape formed peripherally on the external surface of the stimulation catheter.

At least one (e.g., each) intravascular electrode of the stimulation catheter may present a length above 0.5 mm, and/or below 2.5 cm, for example a length between 5 mm and 10 mm. Additionally or alternatively, at least one (e.g., each) intravascular electrode of the stimulation catheter may present a width above 0.3 mm, and/or below 2.5 mm, for example a width between 2 mm and 2.3 mm. A larger area provides an improved contact area that allows the flow of a larger electrical current, thereby allowing a robust and stable stimulation of the phrenic nerve. A good trade-off between flexibility and electrical transmission is achieved with a length between 5 mm and 10 mm and a width between 2 mm and 2.3 mm.

The stimulation catheter may include one or more radiopaque markers, so as to correctly position the one or more intravascular electrodes, for example via fluoroscopy imaging. Additionally or alternatively, such positioning may be achieved via electrical mapping.

The stimulation catheter may include only one intravascular electrode, or alternatively several intravascular electrodes. The case of several intravascular electrodes yet improves the stimulation. The stimulation method may notably comprise operating several intravascular electrodes in a bipolar mode with the patch. This improves stability, by yet enlarging the electric field and likeliness to stimulate the phrenic nerve. Additionally or alternatively, the stimulation method may comprise selecting one or more of the several intravascular electrodes for operation in a bipolar mode with the patch. The selected one or more of the several intravascular electrodes may be intravascular electrodes meeting any predetermined criterion, for example related to quality of the stimulation, e.g., a predetermined criterion relative to positioning (for each selected intravascular electrode). For example, the stimulation catheter may additionally comprise markers of radiopaque material arranged close to the intravascular electrodes. For instance, only intravascular electrodes in contact with the inner wall of the vena cava region vessel may be selected. These electrodes are most appropriate to perform the stimulation efficiently and stably, as further discussed later with reference to the optional expandable portion of the stimulation catheter. The stimulation method may comprise determining such electrodes with any technique, for example by electrical mapping. The presence of several intravascular electrodes thus offers flexibility to the operator and thereby makes the positioning of the stimulation catheter easier. Additionally and/or alternatively, the stimulation method may comprise determining such electrodes via fluoroscopy imaging, thereby making the position of the stimulation catheter particularly ergonomic for the operator.

The case of the stimulation catheter including several intravascular electrodes is now further discussed.

The several intravascular electrodes may comprise more than five electrodes. This yields strong stimulation of the phrenic nerve. Additionally or alternatively, the several intravascular electrodes may comprise less than twenty electrodes. This allows spacing apart of the electrodes. For example, the intravascular electrode may comprise eight, nine, ten, eleven, or twelve electrodes. This provides a good compromise.

The several intravascular electrodes may be spaced apart along the stimulation catheter. This allows maintaining mechanical flexibility of the distal end of the stimulation catheter. The several electrodes may be spaced apart by a predetermined and constant distance, or by a varying distance. In both cases, the distance between pairs of consecutive electrodes may be above 4 mm. This allows a relatively high mechanical flexibility. Additionally or alternatively, the distance may be below 18 mm. This yields strong stimulation of the phrenic nerve. The distance may be of about 9 mm, as this provides a good trade-off between mechanical flexibility and stimulation strength.

The above-mentioned sizes, numbers, spacings of the intravascular electrodes make them well-adapted for electrical stimulation and in particular phrenic nerve stimulation.

The several electrodes may comprise a plurality of electrodes electrically connected together, thus only able to form a single pole. Optionally, the plurality of electrically connected electrodes may be supplied via a single common electrical lead (e.g., electrical wire or conductive path). One may alternatively speak of a single "discontinuous" electrode, although the present disclosure rather refers to a "plurality" of electrically connected electrodes. The plurality of electrically connected electrodes may be obtained for example by covering a portion of the stimulation catheter with a metallic layer, and discontinuously covering the metallic layer by insulating pads. Alternatively, the plurality of electrically connected electrodes may be obtained for example by covering a portion of the stimulation catheter with a metallic layer, covering the metallic layer with an insulating layer, and then forming a discontinuous set of apertures on the insulating layer. The insulating layer may be arranged to cover the external surfaces that are not facing or in contact with the inner wall of the vena cava region vessel. For instance, in the later-provided examples of one or more intravascular electrodes arranged on an expandable portion of the catheter, the insulating layer may cover the surfaces inside the expandable portion, in contact with blood rather than body tissue. Additionally or alternatively, the insulating layer may insulate one or more whole sections of the catheter.

Additionally or alternatively, the several electrodes may comprise a plurality of individual electrodes electrically disconnected one from the other and thus operable independently one from the other. Optionally, each such individual electrode may be supplied via its own dedicated electrical lead (e.g., electrical wire or conductive path), such that the stimulation system may comprise a plurality of electrical leads (e.g., electrical wires and/or conductive paths) each dedicated to a respective electrode. The stimulation system may be configured for selectively operating individual electrodes each in a bipolar mode with the extracorporeal electrode patch, and the stimulation method may comprise such selective operation. Additionally or alternatively, the stimulation system may be configured for selectively operating groups of individual electrodes such that they form a single pole operable in a bipolar mode with the extracorporeal electrode patch, and the stimulation method may comprise such selective operation. By "selective operation", it is meant that the stimulation method comprises selecting one or more electrodes for connection of the selected electrode(s) to the energy source and then supply of energy. Optionally, the stimulation method may alternate between different selective operations, with different individual electrodes or groups of individual electrodes being selected and operated alternatively. Yet additionally or alternatively, the stimulation system may be configured for operating the plurality of individual electrodes altogether such that they form a single pole operable in a bipolar mode with the extracorporeal electrode patch, and the stimulation method may comprise such operation.

In some examples, the one or more intravascular electrodes may comprise a plurality of electrodes, the system being configured for operating the plurality of electrodes so as to deliver simultaneously an electric pulse between each respective electrode of the plurality of electrodes and the extracorporeal electrode patch. In such an example, the plurality of electrodes may comprise between five and twenty electrodes, for example, ten electrodes.

By "operating the extracorporeal electrode patch in a bipolar mode with the one or more intravascular electrodes", it is meant that the extracorporeal electrode patch may form one pole and the (selected) intravascular electrode(s) may form another pole, thus creating an electric field between the two poles. For example, the extracorporeal electrode patch may form the cathode while the one or more intravascular electrodes may form the anode. Alternatively, the extracorporeal electrode patch may form the anode while the one or more intravascular electrodes may form the cathode. Optionally the stimulation system may be configured for alternating polarity of the extracorporeal electrode patch and of the one or more intravascular electrodes.

The extracorporeal electrode patch may be any medical patch or pad comprising a conductive surface configured to be connected to a potential so as to form one single pole, to be positioned in contact with the back or right side of the patient, and to remain substantially fix during the stimulation method. The conductive surface allows the patch to be in a surface contact with the patient, rather than a point contact such as with an electrode pencil or an electrode stylet. The patch thus enlarges the electric field created between the one or more intravascular electrodes, relative to a single-point return electrode or neutral electrode. The patch may be configured for single-use or for multiple-use.

The conductive surface may comprise a conductive substrate configured to be in direct contact with the patient's skin. The conductive surface may present any shape. For example, the conductive surface may consist of a single conductive zone, wherein each pair of points of said single zone are connected by at least one conductive continuous path. Alternatively, the conductive surface may comprise several (e.g., two, three or four) such conductive zones, separated one from the other by non-conductive zones. In such a case, the conductive zones may be connectable altogether to a potential so as to form one single pole operable in a bipolar mode with the (e.g., selected) one or more intravascular electrodes. Optionally, the conductive zones may be selectively connectable to a potential so as to form one single pole operable in a bipolar mode with the (e.g., selected) one or more intravascular electrodes. In examples, the stimulation system may be configured for selectively operating any combination of intravascular electrodes in a bipolar mode with any combination of separate conductive zones of the patch.

Optionally, the single zone or at least one (e.g., each) of the several zones may be substantially plain. Alternatively (respectively, additionally or alternatively), the single zone (respectively, at least one—e.g., each—of the several zones) may form a mesh, for example a regular or irregular grid. In all cases, the conductive substrate may occupy optionally more than 10%, 20%, 50%, 75% or 90% of the convex hull of the whole conductive surface.

The conductive surface may present any geometry, for example any elongated shape with a length higher than a width, such as a generally rectangular shape, or yet a generally elliptic shape. By "length" respectively "width" of the conductive surface, it is meant the maximal respectively minimal Euclidian distance between a pair of points of the conductive surface when the patch is affixed to a plane. An elongated shape allows the extracorporeal electrode patch to be affixed, in the stimulation method, such that the extracorporeal electrode patch extends along the back or right side of the patient (i.e., vertically on the patient's back), or alternatively laterally. This improves stability and robustness of the phrenic nerve stimulation.

The conducting surface may present dimensions high enough to improve stability and robustness of the phrenic nerve stimulation. In particular, the conducting surface may present a length higher than 1 cm, 2 cm, 4 cm, 8 cm, 12 cm. Additionally or alternatively, the conducting surface may present a width higher than 1 cm, 2 cm, 3 cm, 4 cm, 5 cm. For example, the conducting surface may present a length higher than 1 cm and a width higher than 1 cm, or the conducting surface may present a length higher than 2 cm and a width higher than 1 cm, or the conducting surface may present a length higher than 4 cm and a width higher than 2 cm, or the conducting surface may present a length higher than 8 cm and a width higher than 4 cm, or the conducting surface may present a length higher than 12 cm and a width higher than 4 cm, or the conducting surface may present a length higher than 12 cm and a width higher than 5 cm.

The conductive surface may present dimensions low enough to facilitate affixing to the patient's back. In particular, the length of the conductive surface may be smaller than 40 cm or 30 cm, and/or the width of the conductive surface may be smaller than 30 cm or 20 cm. For example, the conductive surface may present a length smaller than 40 cm and a width smaller than 30 cm, or a length smaller than 30 cm and a width smaller than 30 cm, or a length smaller than 30 cm and a width smaller than 20 cm.

For instance, the conductive surface may present a length between 15 cm and 25 cm, and a width between 5 cm and 15 cm, such as a length of about 20 cm and a width of about 10 cm. Optionally, the conductive substrate may occupy more than 75% of the convex hull of the whole conductive surface, for example more than 90%.

The patch may comprise a conductive layer applied to the skin of the patient. The conductive layer may be made of any electrically conductive material, such as a metallic material, a conductive gel, or yet a conductive rubber. The conductive gel layer may be supported by a silicone layer. The patch may optionally have an external insulating layer opposite to the conductive surface, such as the silicone layer itself (thus insulating), or an extra layer, for example made in a plastic or fabric material. The patch may comprise an electrical connector (e.g., a plug or one or more tabs) for (e.g., removably) connecting an electrical cord or cable to the conductive layer. The electrical cord or cable may allow connection to an energy source, in particular to a potential thereof. Alternatively, the patch may comprise non-removably such an electrical cord or cable.

The conductive layer may be made of a flexible material, and the patch itself may be flexible. In case the conductive layer is made of a metallic material, the metallic material may be a flexible metallic sheet. The flexibility allows following the shape of the body of the patient, and thus improve stability and robustness of the phrenic nerve stimulation, thanks to the surface being in better contact with the body of the patient. Alternatively, the patch may consist of a rigid plate, for example a rigid metal plate, optionally with a top layer made of a conductive gel, and the patient may lie with the back on the plate (on top of the gel layer if any). Thanks to the patient's weight, a relatively good contact may still be achieved between the patient's back and the plate.

The patch may further comprise an adhesive coating, thereby making the extracorporeal electrode patch is self-adhesive. This allows the patch to remain well-affixed to the patient's back during the procedure. The adhesive coating indeed impedes movement of the patch during medical intervention, in particular during phrenic nerve stimulation. Also, the operator may quickly attach the patch to the patient, without further fixation elements, or additional adhesives. The adhesive coating may be conductive and cover partly or fully the conductive layer. This improves maintaining of the patch in place. Alternatively, the adhesive coating may surround the conductive layer.

Thus, as noted, the conductive surface may either be the surface of the conductive layer non-coated and thus against the patient's skin, or the surface of a conductive adhesive coating if any. Further, as noted, the expression "affixed to the patient" only means that the patch remains in a substantially fixed position relative to the patient's body during the procedure. This may optionally be achieved by attachment of the patch to the patient's back, such as by adhesion as explained above or by any other means (such as taping or wrapping the patient's upper body with clothing), but not necessarily.

An example of a self-adhesive metallic patch covered with a plastic external layer which was used in the experiments later-discussed is the following product: NESSrPlate 170, split, by Erbe. This patch has a conductive surface split in two separate conductive zones. The patch has a total area 168 cm$^2$, and a generally rectangular shape of a length of about 20 cm and of a width of about 8 cm.

The stimulation catheter is configured for being introduced and operated in the superior vena cava. The stimulation method may be minimally invasive, and the stimulation catheter may thus be configured for being introduced for example through the femoral vein. The stimulation catheter is thus flexible enough, long enough, and with a small enough diameter. For example, the stimulation catheter's outer diameter may be equal or above to 4 Fr, and/or below or equal to 10 Fr, for example 6 Fr, 7 Fr or 8 Fr. The catheter's length may be above 90 cm and/or below 200 cm, for example equal to about 145 cm.

The stimulation catheter may comprise positioning means.

For example, the stimulation catheter may comprise a (e.g., metallic) guidewire configured for guiding the catheter to the vena cava. The guidewire may be arranged in an internal lumen of a body of the catheter and exit a distal extremity of the catheter body. The guidewire may present a diameter above 0.020" and/or below 0.060", preferably above 0.030" and/or below 0.040", for example equal to 0.032" or to 0.035". The guidewire may be inserted in a hemostatic valve. The stimulation catheter may further comprise a flushing lumen. In an example, the guidewire is made of a hydrophobic material.

Alternatively, the stimulation catheter may have a body which comprises an internal lumen configured for insertion of a positioning mandrel. The lumen may be closed at the distal end of the catheter body, such that the mandrel cannot exit the catheter body. The stimulation catheter may additionally comprise such mandrel.

Figure 2:
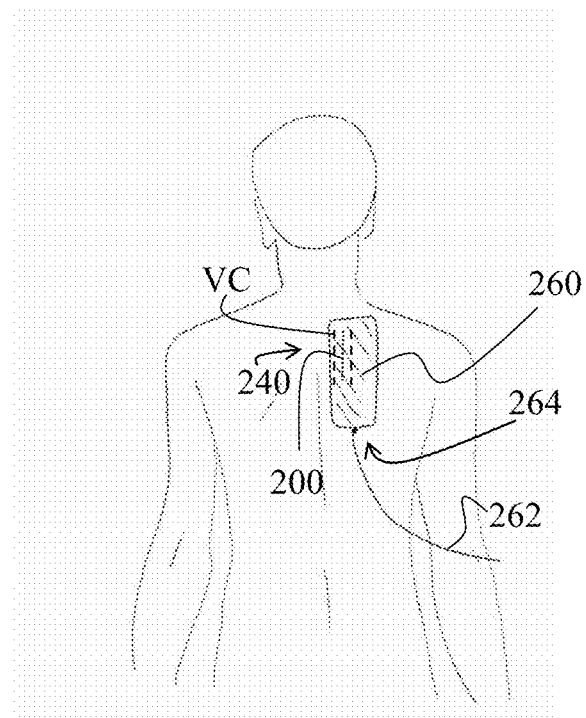
FIG. 2 illustrates an example of the stimulation method with an example of the stimulation system.

FIG. 2 illustrates an example the stimulation method with a schematic example of the stimulation system. As shown, an operator may perform the stimulation method by affixing an extracorporeal electrode patch 260 to the back of a patient. In particular and as visible on the figure, patch 260 may be of a generally rectangular shape and/or with a length higher than a width, and the stimulation method may comprise affixing patch 260 such that it extends along the back of the patient. In specific, patch 260 may be affixed at the right paraspinal, facing the inner part of the right scapula, and go up to the tip of the right shoulder blade. In variations, the patch 260 may be affixed such that it extends laterally on the back of the patient, and/or anywhere else opposite to the distal portion 240 relative to the phrenic nerve. As schematically illustrated, the method may comprise introducing the distal portion 240 of a stimulation catheter 200 into the superior vena cava VC of the patient. The stimulation catheter 200 is located in a position where its distal portion 240 faces the phrenic nerve (not illustrated) across patch 260. In this position, the phrenic nerve is located between distal portion 240 of the stimulation catheter 200 which carries one or more intravascular electrodes (not illustrated) and patch 260. Therefore, by using an energy source (not illustrated) having one pole in electrical communication with the intravascular electrodes of the distal portion 240 and another pole in electrical communication with the patch 260 via an electrical cord 262, an electrical field may be created therebetween. The electrical field closes a circuit that crosses the phrenic nerve. Therefore, the phrenic nerve can be stimulated. Thanks to the spread area of the conductive surface of patch 260, the phrenic nerve can be captured easily, robustly, and stably. This provides high ergonomics of use to the operator who may only need to adjust the stimulation catheter 200 to an intravenous position to start the electric field. This may also allow a more secure cryoablation method, by making monitoring of diaphragmatic contraction response more reliable.

Figure 3:
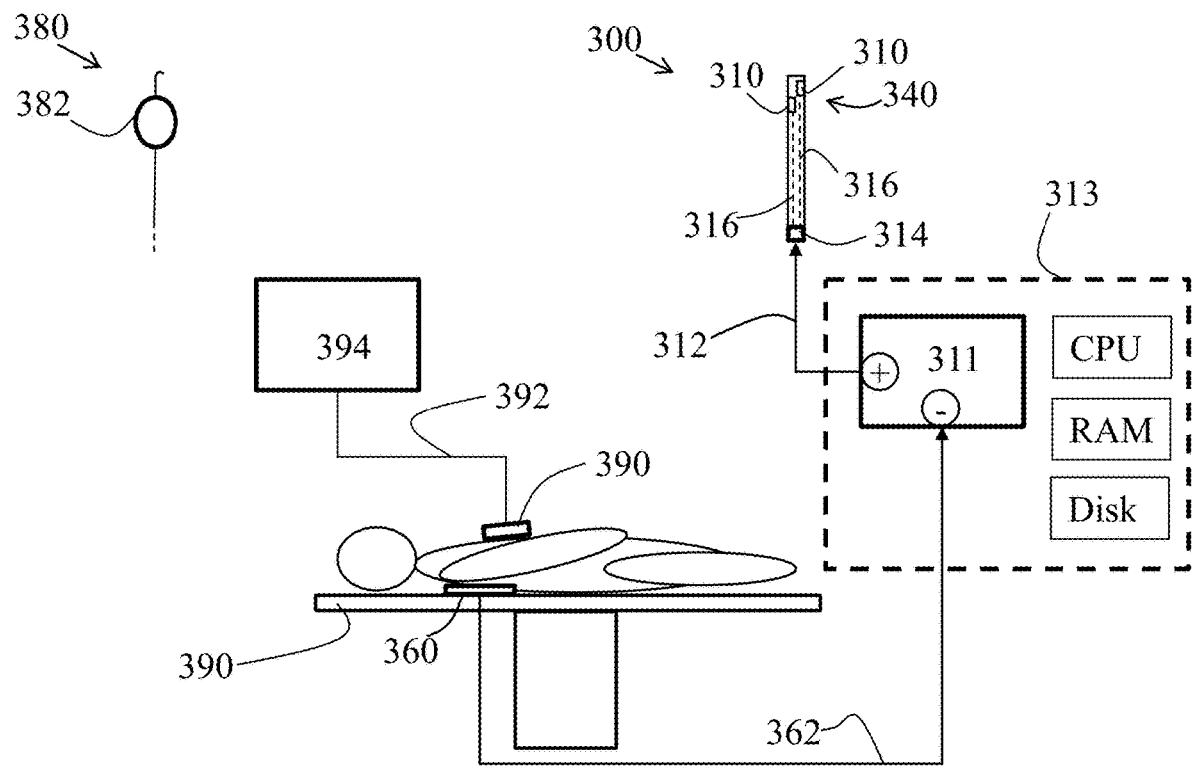
FIG. 3 shows an example of the cryoablation system.

FIG. 3 shows an example of a cryoablation system comprising the stimulation system and used during a cardiac cryoablation method performed on a human patient, wherein the cryoablation method includes performing the stimulation method repeatedly throughout the cryoablation procedure.

The stimulation system comprises a stimulation catheter 300 including one or more intravascular electrodes 310 arranged on a distal portion 340 of the catheter, an extracorporeal electrode patch 360, and optionally an energy unit 313 including an energy source 311. Energy source 311 is connectable to stimulation catheter 300 via an electrical cord 312 and an electrical connector 314 of stimulation catheter 300, so as to supply the electrodes 310 via electrical leads 316 respective to each intravascular electrode 310 (or alternatively, in case of several intravascular electrodes 310, a common single lead electrical). Energy source 311 is further connectable to patch 360 via an electrical cord 362. Thus, energy source 311 is configured to operate patch 360 and intravascular electrode(s) 310 in a bipolar mode.

The energy unit 313 may optionally comprise a processor, such as a CPU, coupled to memory, such as non-volatile memory—e.g. hard disk—and/or RAM, and the processor may be configured for controlling the energy source 311, so as to deliver electric pulses that are configured for phrenic nerve stimulation, as earlier-described. For that, the memory may have recorded thereon a computer program comprising code instructions for operating the energy source 311.

The computer program may comprise instructions executable by the processor, the instructions comprising means for causing the above system to perform the electric pulse deliver of the stimulation method. The program may be recordable on any data storage medium. The program may for example be implemented in digital electronic circuitry, or in computer hardware, firmware, software, or in combinations of them. The program may be implemented as an apparatus, for example a product tangibly embodied in a machine-readable storage device for execution by a programmable processor. The application program may be implemented in a high-level procedural or object-oriented programming language, or in assembly or machine language if desired. In any case, the language may be a compiled or interpreted language. The program may be a full installation program or an update program.

The cryoablation method may comprise affixing patch 360 to the human patient, laying the patient on his back over an operating table 390, introducing the stimulation catheter 300 in the superior vena cava of the patient, for example via a minimally invasive procedure.

The cryoablation method may further comprise providing a cryoablation catheter 380, such as a cryoballoon catheter. The cryoablation-catheter may be a cryogenic balloon catheter 380 having a balloon 382 for cryoablation. The cryoablation method further comprises introducing cryoballoon catheter 380 inside the left atrium of the patient's heart, for example via a minimally invasive procedure (e.g., through the femoral vein of the patient). The cryoablation method then comprises performing cryoablation (i.e., cold ablating body tissue), and meanwhile (i.e., substantially simultaneously), operating patch 360 and intravascular electrode(s) 310 in a bipolar mode with the energy source 311 so as to repeatedly stimulate the patient's phrenic nerve, for example by delivering pulses of the order of 10V amplitude of the order of a few ms duration, and at a frequency of the order of 60 pulses per minute (1 pulse/s).

The stimulation system may further comprise a unit for monitoring a diaphragmatic response to phrenic nerve stimulation, for example via objective analysis. The unit may for example comprise a sensing module 390, such as a CMAP (compound muscle action potential) sensing means or a gravitometer, e.g., installed on the patient's chest/abdomen. The unit may further comprise a communication means 392, such as a cable or a wireless module, to send measurements to a monitoring module 394. Monitoring module 394 may comprise any means to output a representation of the received measurements to the operator, such as a display, an alert generator (e.g., the alert may be visual and/or an audio cue), and/or a printer (for example adapted for transcription of the received measurements into a graph, e.g., printed on millimeter ECG paper). Thanks to such a monitoring unit, contraction of the diaphragmatic dome in response to the phrenic nerve stimulation may be observed objectively, thus particularly accurately. Alternatively, the contraction of the diaphragmatic dome may be assessed with abdominal palpation.

In case the response decreases, this means that an injury of the phrenic nerve is upcoming. The cryoablation method may comprise taking this into account. For example, the cryoablation may be paused, for instance upon or very soon after the observation of the response decrease (e.g., less than 20 s, 10 s, or 5 s after such observation). The cryoablation may be resumed only after observation that the response has retrieved its base line state, meaning that the phrenic nerve has recovered.

Thanks to the stimulation system improving stability of the phrenic nerve stimulation, the cryoablation method is more secure with respect to phrenic injury and/or faster to perform since the monitored diaphragmatic response's reliability is improved.

The systems disclosed herein may be provided within a kit for phrenic nerve stimulation. The kit comprises the stimulation system or the system for cardiac cryoablation. The kit further comprises instructions (e.g., recorded on a physical support) for phrenic nerve stimulation of a human patient, for example during cardiac cryoablation. For example, the kit may comprise a paper support, such as a handbook or a leaflet, with instructions in the form of text and/or pictograms thereon. Alternatively, the kit may comprise a computer-readable medium, such as a USB, having recorded thereon such text and/or pictograms in a computer file. Yet alternatively, the instructions may be downloadable, for example at a URL indicated on any physical support of the kit. The instructions may explain a procedure for phrenic nerve stimulation, and the instruction may optionally mention cryoablation. Optionally, the kit may further comprise instructions for monitoring a diaphragmatic response to phrenic nerve stimulation and/or instructions for performing a cardiac cryoablation. In other words, the instructions may comprise a description of any example of the stimulation method or of the cryoablation method disclosed herein.

In examples, the distal portion of the stimulation catheter may comprise an expandable portion, and accordingly the stimulation catheter may have both an expanded configuration and a non-expanded configuration. By "expandable portion", it is meant that the portion is deformable such that its diameter (i.e., maximal width of the portion in a direction orthogonal to the catheter's longitudinal axis, that is, the cava vein's longitudinal axis) may be increased relative to the catheter's diameter (i.e., the diameter of the non-expandable parts of the catheter), possibly until fitting the vein's internal walls. The maximal diameter of the expandable portion (i.e., when fully expanded) may be above at least five times or even ten times the diameter of the catheter. The expandable portion may comprise the distal end of the distal portion of the stimulation catheter, which is thus displaceable relative to the catheter's longitudinal axis. Alternatively, the expandable portion may be formed and end at a proximal location distinct from the distal end of the stimulation catheter, which may thus remain on the catheter's longitudinal axis when the expandable portion is expanded. The stimulation catheter may be reversibly deformable between the expanded configuration and the non-expanded configuration. Thus, the operator may deploy the expandable portion to expand the stimulation catheter inside the vena cava region vessel, operate the catheter, and afterwards straighten back the expandable portion into the non-expanded configuration so as to pull out the catheter.

The stimulation catheter may be adjustably expandable. The operator may thus adjust the expandable portion to maintain the distal portion in a firm position of the vena cava, in particular a position wherein the distal portion is relatively close to the phrenic nerve. Alternatively, the expandable portion may be automatically expandable. In such a case, the expansion may only be triggered, and the catheter may self-deploy into the expanded configuration.

The expandable portion may be configured to fit the inner wall of the vena cava or the inner wall of the right subclavian vein, for example circumferentially.

By "fit" the inner wall of a vein (i.e., any of the inner tissues branching from the vena cava to the right subclavian vein or brachiocephalic veins), it is meant that the expandable portion is configured to expand and achieve at least the diameter of the vein, so as to contact the inner wall of the vein and remain stable in position. For example, the expandable portion may present a diameter above 10 mm, 20 mm, 25 mm, 30 mm, 35 mm or 40 mm, for example of the order of 50 mm. This allows fitting the vena cava region vessel. The larger values of the expandable portion's diameter allow a more secure fit, in particular in the vena cava. The expansion may be adjustable. Thus, the operator may be enabled to deploy the expandable portion in the vena cava region vessel and adjust the expandable portion to the size thereof. Alternatively, the expansion may be non-adjustable, and for example triggering the expansion may allow the diameter to increase until constrained by the inner wall of the vena cava region vessel. The expandable portion may be made in a relatively soft material (for example as the rest of the catheter), and thereby fit the vena cava region vessel with no harm thereto. Thanks to the expandable portion, the stimulation catheter is easier to maintain in place and stable during operation, thereby improving ergonomics and stability of the phrenic nerve stimulation. The expandable portion may for instance have a diameter between 10 mm and 35 mm in the expanded configuration.

By "circumferentially fit", it is meant that the expandable portion fits a cross-sectional circular area of a volume. In other words, the expandable portion itself does not necessarily have a solid circle or a cylindrical or spherical volume, but it is appropriate to fit a cross-sectional circular area. Thus, the expandable portion is well suited for fitting the walls of a vein, which presents cross-sectional circular areas in the inner walls. This improves positional stability of the catheter. Indeed, the operator may expand the expandable portion within the walls of the vein (e.g., by manual adjustment or triggering of automatic deployment). The cryoablation method may then comprise performing cryoablation while the catheter self-remains in a stable position. Thus, the operator may operate, simultaneously while performing the cryoablation, the patch and intravascular electrodes of the catheter so as to stimulate the patient's phrenic nerve repeatedly and robustly thanks to the stable positioning.

The circumferential fit may be such that the catheter remains in position. In other words, the maximal diameter of the expandable portion may be higher than the diameter of the superior vena cava, of the right brachiocephalic vein, and/or of the right subclavian vein, such that a certain level of friction is achieved when the expandable portion is expanded, and the catheter thus substantially remains in place during its operation (unless a significant force is applied to overcome the friction). The expandable portion thus acts as an anchoring portion. The fitting indeed allows the vessel to retain the expandable portion, thus acting as an anchor.

In examples, at least one (e.g., several or all) intravascular electrode may be arranged on the expandable portion. This allows such electrode to be closer to the inner wall of the vena cava region vessel, thereby improving electrical connection and thus phrenic nerve stimulation stability. In particular, at least one (e.g., several or all) intravascular electrode may be arranged on the expandable portion so as to be in contact with an inner wall of the vena cava region vessel when the catheter is in the expanded configuration. By "in contact", it is meant that there is no gap that allows the flow of blood between the intravascular electrode and the inner wall. In other words, the intravascular electrode has a position, orientation and dimension in the expandable portion so that at least one intravascular electrode is in contact with the inner wall of the vena cava region vessel. Thus, electrical conductance between the catheter and the extracorporeal patch is improved, in contrast to having blood passing between the electrode and the wall of the vein. Therefore, stability of the phrenic nerve stimulation is yet improved. In particular, for optimal stability of the electrical field and to yet improve operation in bipolar mode with the extracorporeal electrode patch, all intravascular electrodes may be arranged to be in contact with the inner walls of the vena cava or the right subclavian vein.

In examples, the one or more intravascular electrodes may be positioned circumferentially on the expandable portion. By "positioned circumferentially" it is meant that each of the one or more intravascular electrodes are arranged along a diameter of a cross-sectional area of the expandable portion. In other words, each of the one or more intravascular electrodes are separated by a circumferential distance along a cross-sectional view of the walls of the expandable portion.

The arrangement along the diameter may occupy the whole of the diameter or a portion thereof. The extent of the positioning may be measured by the angle between a first end a second end positions of the expandable portion defining the beginning and the end of the positioning along the diameter. The first end and the second end may be chosen by convention. An angle of 360 degrees between the first end and the second end (i.e., the same position) from the center of the circumference means that the arrangement covers the whole circumference. One or more intravascular electrodes may be arranged between the first and second end.

In examples, the one or more intravascular electrodes may be arranged at an equidistant angle with respect to each other and the first and second end, e.g., ten intravascular electrodes. In other examples, the intravascular electrodes may be placed with different angles. For example, the intravascular electrodes may be closer to each other in a middle section between the first and second endpoints. The circumferential positioning of the one or more intravascular electrodes may be arranged in different longitudinal positions along the volume or area covered by the expandable portion, and possibly other intravascular electrodes arranged on non-expandable portions of the stimulation catheter.

For example, several longitudinal rows, e.g., each along the catheter's axial direction are positioned circumferentially. In another example, three rows may be separated by a circumferential angle of 120°, or four rows separated by a circumferential angle of 90°. In yet another example, the rows may be separated by different angles, e.g., three rows separated by angle of 60° and two rows separated by a circumferential angle of 90°.

The circumferential positioning allows making sure that at least one electrode or row of electrodes is substantially facing or nearly facing the walls of the superior vena cava in front of the phrenic nerve, and thereby to ensure that the electrodes are near the phrenic nerve. In general, the stimulation method may comprise positioning at least one (e.g., several or all) intravascular electrode against a portion of the inner wall of the vena cava which faces the phrenic nerve. In other words, there exists a straight path from the nerve to said portion, without encountering, e.g., first another portion of the vena or another kind of tissue that obstructs the inner wall of the vena cava to be in the straight path of the nerve. By positioning in this manner, the operator ensures that the electrical field, or at least some electric fields thereof, will directly stimulate the phrenic nerve, thereby providing the stimulation necessary to evaluate diaphragmatic monitoring. When the distal portion comprises an expandable portion carrying one or more intravascular electrodes positioned circumferentially, such a positioning is very ergonomic as the operator only needs to trigger or adjust the expansion of the portion to achieve a correct positioning of at least one or a row of electrodes. As a result, the stimulation is more secure. As mentioned above, a mapping may allow selecting such well-positioned electrode(s) for exclusive operation thereof, so as to improve efficiency. Alternatively, radio opaque material can be used to correctly positioned the catheter.

Additionally or alternatively to being expandable, the stimulation catheter may be deflectable at its distal portion. By deflectable, it is meant that the distal portion may be bent at least in one direction with respect to the body of the catheter. The maximal bending may be above 10 degrees and/or below 90 degrees. In examples, the maximal bending may be above 25 degrees, so as to allow positioning of the expandable portion to the right subclavian vein. The stimulation catheter may comprise a pull-wire to impart deflection.

In an example, the catheter may comprise a non-expandable distal end after the expandable portion. In other words, the non-expandable distal end does not expand and so remains in its original shape when the catheter expands. In a particular example, the non-expandable distal end may be straight, and stay straight in the axis of the catheter (i.e., the axis of the vena cava region vessel) even when the catheter is in the expanded configuration. The non-expandable distal end may for example have a length higher than 1 cm, and/or lower than 12 cm, for example between 1.5 cm and 4 cm.

Examples of the expandable portion are now discussed. The expanded configuration may be a helical (i.e., spiral) configuration, a loop configuration, a lasso configuration, an umbrella configuration, or a basket configuration. Such examples present the common point that the expanded portion may comprise blood flow passages when expanded, so as to reduce risks of obstruction of blood flow due to expansion of the catheter.

By "helical/spiral configuration" it is meant that the material of the expandable portion has a shape formed by one or more helical coil segments connected in series between a proximal endpoint of the distal portion and another endpoint, farther in a longitudinal distance from the endpoint of the distal portion. Each of the one or more helical coil segments consists of one or more turns of the material of the expandable portion around a cylinder. For example, the material of the expandable portion may be a wire-like material or a flexible material that is adapted to adopt such a configuration. The helical configuration thus presents an open volume defined by the cylindrical volume inside the inner volume of the helical coil segments and the endpoints, wherein the helical coil segments may be in contact with the walls of the inner wall of the vena cava region vessel and blood flow is unobstructed. The helix of a helical configuration may be of constant or varying diameter. The helical configuration is sometimes known as a "spiral configuration", although the present disclosure gives a different meaning to the latter term, as explained below.

In an example, the helix or spiral formed by the expandable portion may have at most two coils in the expanded configuration, in other words, any fraction of a number of coils (a "coil" or "spire" being a portion of the helix or spiral corresponding to exactly one turn) below or equal to two, for example (exactly) one coil, one and a half coils, or two coils. A maximum of two coils provides simplicity of manufacture and use and yields low cumbersomeness, as the addition of more coils may result in an overly complex structure that risks losing its initial shape. In a particular example, the catheter may comprise a (e.g., straight) non-expandable distal end portion and the expandable portion may comprise at most two coils in the expanded configuration. Such examples may facilitate operation of the system in that the double coil can recover its shape after insertion and the non-expandable distal end can enable the double coil to maintain its desired shape. The non-expandable distal end may not only improve the positioning of the double coil but also its repositioning in the vena cava region vessel. The non-expandable distal end portion compensates the impact on stability of a reduced number of coils.

In further examples, the helical or spiral configuration may have a pitch or height of one complete helical or spiral turn between 5 mm and 15 mm. An increased pitch may assist maintaining the original shape of the helical or spiral configuration upon removal of a positioning means. In another example, an increased pitch in the helical or spiral configuration may be supported by the presence of a non-expandable distal end. In other words, the non-expandable distal end may assist the configuration in maintaining such an increased pitch.

By "loop configuration" it is meant that the material of the expandable portion has a closed shape that follows a circular, or substantially circular (e.g., elliptical) shape. The shape thus follows a closed circular or elliptical path that remains in contact with the walls of the inner wall of the vena cava region vessel and maintains an open space in between, thereby allowing the flow of blood through the expandable portion. The loop may be contained in any plane, for example a longitudinal plane of the catheter or a cross-section plane (e.g., orthogonal to the longitudinal axis of the catheter).

By "lasso configuration" it is meant that the material of the expandable portion has a closed shape that follows a helical shape of at most one turn from a base in a proximal endpoint of the distal portion. The shape thus follows a circular path that maintains in contact with the walls of the inner wall of the vena cava region vessel an open space in between, thereby allowing the flow of blood through the expandable portion. The lasso may be contained in any plane, for example a longitudinal plane of the catheter or alternatively a cross-section plane (e.g., orthogonal to the longitudinal axis of the catheter).

By "umbrella configuration" it is meant that the expandable portion consists of more than one segments that extend radially outwards from an endpoint on a proximal end of the distal portion. The outmost endpoints of the segments may be connected by a mechanism that stabilizes the segments in the expanded position. For example, the mechanism may stretch the one or more outmost endpoints along a circumference. The space between the segments remains unobstructed, thereby allowing the flow of blow through the expandable portion.

By "basket configuration", it is meant that expandable portion consists of one or more segments each interconnected between a proximal endpoint of the distal portion and a farther endpoint from a longitudinal distance from the endpoint of the distal portion. Each of the segments is disposed at a different angle of each other with respect to the endpoint of the distal portion. Each of the segments preserves the same angle at the farther endpoint. In the expanded configuration, each of the segments follows a circumference between both endpoints. The segments may have a width that maintains an open space between each of the segments, thereby allowing the flow of blood. Thus, this configuration allows a contact with the inner wall of the vena cava region vessel without obstructing the flow of blood.

The stimulation catheter may further comprise one or more mechanisms, actionable by the operator, for deforming the expandable portion of the stimulation catheter from the straight configuration into any of the expanded configurations described above. For example, the stimulation catheter may comprise one or more pull-wires, actionable for deforming the stimulation catheter into the expanded configuration, and optionally a handle to manipulate the one or more pull-wires. By action of the operator, the pull-wires may deform the expandable portion via an appropriate mechanism that expands the expandable portion. Such mechanisms provide high ergonomics of use to the operator to adjust the stimulation catheter to the walls of the vena cava region vessel, which may vary depending on multiple factors. The operator may adjust the expandable portion prior to performing the stimulation of the phrenic nerve in base of his medical assessment, to permit a deployment of the stimulation catheter to perform a stable electrical stimulation. Additionally or alternatively, the expandable portion may be at least partially made of a shape memory material. The shape memory material may thus bias the expandable portion into the expanded configuration. The expansion in such a case may be triggered in any manner. Optionally, the catheter may comprise a retractable sheath covering the expandable portion and/or a retractable inner straightening member (e.g., straightening wire or straightening mandrel, e.g., also serving as positioning means, such as guidewire or positioning mandrel), that straightens the expandable portion to allow insertion of the catheter in the superior vena cava. Retraction of such member allow release of the biasing and automatic expansion of the portion due to the shape memory of the material. Such mechanisms improve positional stability inside the vena.

Alternatively to having an expandable portion, the catheter may be a straight catheter. In such a case, the catheter may optionally be deflectable.

Examples of the stimulation catheter are now discussed with reference to FIGS. 4-10. The discussion of the figures often refers to the superior vena cava, but it applies similarly to other vena cava region vessels as earlier-discussed. In these examples, the stimulation catheter has an expandable portion as discussed above. The examples described hereunder detail several expanded configurations of the stimulation catheter that provide ergonomics of use to the operator for positioning at least one intravascular electrode, and a stable stimulation of the phrenic nerve.

Figure 4:
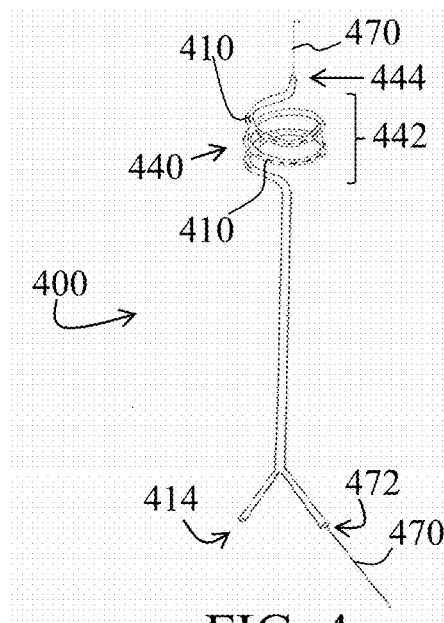
FIG. 4 shows an example of the catheter for phrenic nerve stimulation having an expandable portion.

FIG. 4 shows an example of a stimulation catheter 400 having a helical configuration. The stimulation catheter 400 comprises a distal portion 440, an electrical connector 414 and a lumen entry 472. The lumen entry 472 may be configured, e.g., for introducing a guidewire 470. The guidewire 470 exits the extremity 444 of the distal portion. The guidewire 470 may be configured for the operator to position the distal portion 440 inside the vena cava region vessel. The electrical connector 414 may be connected to electrical leads. The distal portion comprises an expandable portion 442. The expandable portion comprises a plurality of intravascular electrodes 410 arranged circumferentially thereon. Alternatively, the expandable portion may comprise a single elongated electrode extending circumferentially along the expandable portion 440. The expandable portion 442 may be adjusted or self-expanded, so that the intravascular electrodes 410 are positioned in an outward section of the walls of the expandable portion 442 to fit the wall of the vein. Optionally, the material of the extremity 444 may be made of a flexible material serving as a guide. Optionally, the catheter may comprise a retractable sheath (not shown) covering the expandable portion 442 and/or a retractable inner straightening wire (not shown), that straightens the expandable portion to allow insertion of the catheter in the superior vena cava. Retraction of such sheath and/or inner straightening wire may allow expansion of the helix, and/or trigger said expansion. The principle presented on the figure applies to other types of expanded configuration. However, in such cases, the guidewire 470 may sometimes exit the catheter body, notably at the expandable portion, rather than always remain in a lumen formed in the catheter body as is the case on the figure.

Figures 5A, 5B, 6A, 6B:
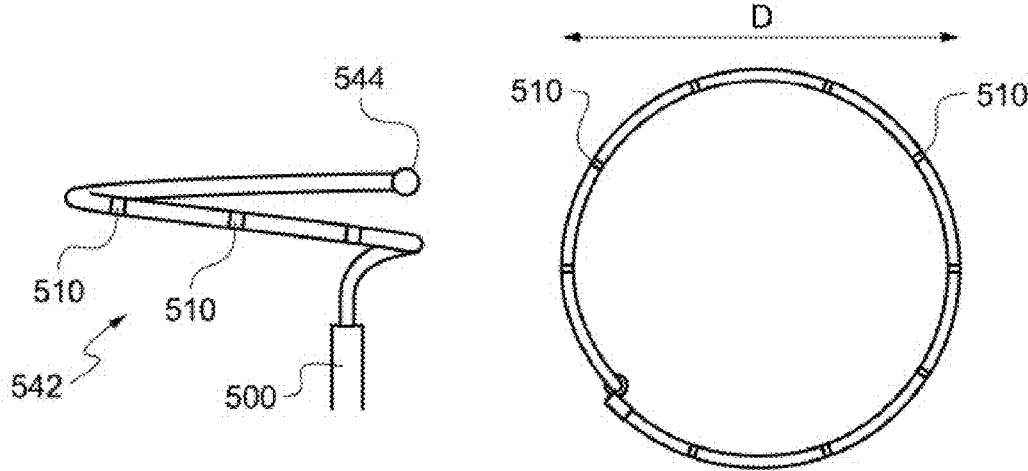
FIGS. 5A-5B show an example of the catheter for phrenic nerve stimulation having a lasso configuration, respectively in a longitudinal view and in a cross-sectional view.
FIGS. 6A-6B show an example of the catheter for phrenic nerve stimulation having a helical configuration, respectively in an expanded configuration and in a straightened configuration.

FIGS. 5A and 5B show a catheter 500 with an expandable lasso portion 542. The expandable lasso portion 542 may be seen as presenting a helical shape of one turn, turning upwards to an endpoint 544. A number of intravascular electrodes 510 are arranged circumferentially on the expandable portion 542, for example with an equidistant spacing. Each of the electrodes 510 is positioned facing an outward direction to maximize contact with the tissue of the vein. The electrodes are arranged between the extremity 544 of the expandable portion 542 and the catheter body 500. The lasso may be compressed or straightened in a non-expanded configuration to allow the insertion on the stimulation catheter. In an expanded configuration, the operator may increase the diameter D of the lasso along the cross-sectional section to fit the walls of the vein, for example with a handle manipulating one or more pull-wires configured for that. This configuration is easily deployed into an expanded configuration by the user, and it remains physically stable. The circumferential arrangement of the electrodes allows the user to position the catheter in any angle in the vena cava.

FIGS. 6A and 6B show another example of a catheter 600 with an expandable helical portion 642, respectively in a helical configuration and in straightened configuration where the helix is stretched.

The helix comprises loops along a longitudinal direction of the expandable portion 642. For example, the helix may comprise between two and five loops. The loops may not need to be complete. For example, the helix comprises two and a half loops. In the straightened configuration, the expandable portion may be covered by a retractable sheath 602. The helix may be expanded by the operator for example through a pull-wire (not shown) connected through the endpoint 620 that retracts the sheath. The expandable portion may be made of a shape memory material. Thus, the operator may retreat the sheath and the material returns the shape of the expandable portion to the helical configuration. The helical configuration may adjust, thanks to the loops of the helix, to the inner walls of the vein to achieve a circumferential fit. The helix may comprise a plurality of electrode 610 that may be arranged along the length of the helix or a portion of a loop, that is, all of the loops of the helix.

As shown on FIG. 6A, each electrode 610 may present a length higher than a width, and the plurality of electrodes 610 may be arranged circumferentially on the expandable portion so as to extend substantially along the vena cava when the stimulation catheter is in the expanded configuration. In other words, each electrode length is arranged substantially longitudinally along the vena. This achieves an efficient electrical field.

FIG. 6B shows schematically the stimulation catheter in a straightened configuration. The electrodes are slightly displaced by a small deviation angle in the straightened configuration compared to the expanded configuration with respect to the same longitudinal axis, due to stretching of the helix. When the stimulation catheter is in an expanded configuration, the electrodes 610 may be aligned in several rows to transmit an electrical field that traverses the phrenic nerve, as the phrenic nerve is substantially along the vena cava. The rows are distributed circumferentially on the vena cava. Alternatively, the electrodes may be dispersed such that no such rows are formed, and still the electrodes cover the circumference of the vena cava. These arrangements provide high ergonomics of use where the user does not need to worry to place directly the expandable portion close to the phrenic nerve. Moreover, the helical configuration allows the operator to fix the expandable portion along the longitudinal section of the walls of the vena cava. Therefore, the stimulation catheter remains in fixed position, improving the stability of the stimulation of the phrenic nerve.

Figure 7:
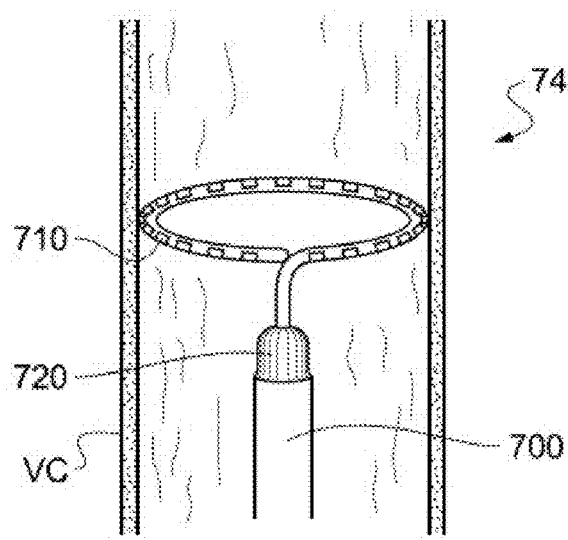
FIG. 7 shows an example of the catheter for phrenic nerve stimulation having a horizontal loop configuration.

FIG. 7 shows another example of a catheter 700 with expandable portion 742, wherein the expanded configuration is a horizontal loop configuration. The horizontal loop is deployed along a plane orthogonal to the longitudinal axis of the walls of the vein. For example, the horizontal loop configuration 742 is deployed orthogonal to the walls of the vena cava VC. This is provided just for the sake of illustration. For example, the horizontal loop configuration 742 is deployed orthogonal to the walls of the right subclavian vein. The expandable portion 742 comprises a horizontal loop segment that loops inwards (in any direction) from the endpoint 720.

When the catheter 700 is in a non-expanded configuration, the loop of the horizontal loop segment may be contracted along the longitudinal direction of the expandable portion and kept inside a sheath, so as to be compact/straight with respect to the stimulation catheter and allow the insertion thereof through the femoral vein. The horizontal may be expanded by the operator with a pull-wire or guide connected through the endpoint 720. The pull-wire or guide may allow a reversible action and the expansion may be performed automatically or manually, thereby providing to the operator the capability of expanding the horizontal loop along the cross-sectional direction to achieve a circumferential fit of the vein.

The operator has high ergonomics of use. The operator can adjust the circumferential fit of the stimulation catheter to the vein VC by adjusting the cross-sectional diameter of the horizontal loop segment. The horizontal loop segment may comprise a single electrode that may be arranged along the length of the horizontal loop segment, that is, all of the loops of the horizontal loop, or a portion thereof, that is, no more than some loops of the horizontal loop segment. Optionally, several intravascular electrodes 710 may be arranged along the horizontal loop. FIG. 7 shows several electrodes arranged only in regions of contact with the walls of the vein VC. The stimulation catheter remains fixed and stable thanks to the horizontal loop segments that adjust to the walls of the vein, thereby improving the stability of the stimulation of the phrenic nerve.

Figure 8:
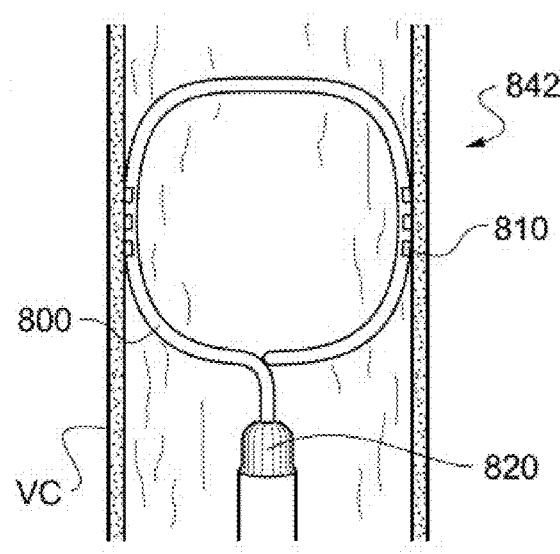
FIG. 8 shows an example of the catheter for phrenic nerve stimulation having a vertical loop configuration.

FIG. 8 shows another example of a catheter 800 with an expandable portion 842, wherein the expanded configuration is a vertical loop configuration. The vertical loop configuration comprises intravascular electrodes 810 that are placed in an outwards face of the vertical loop. FIG. 8 shows the vertical loop 842 expanding along a longitudinal axis of the superior vena cava VC. This positioning is provided only for the sake of illustration, alternatively, the vertical loop may expand along a longitudinal axis of the right subclavian vein. The electrodes 810 are arranged along the longitudinal section of the loop that are in contact with the walls of the vein. The vertical loop may be in a compressed configuration by pulling to the endpoint 820 to allow the insertion on the stimulation catheter. In an expanded configuration, the operator may increase the diameter of the vertical loop (automatically or manually) to fit the walls of the vein.

Figure 9:
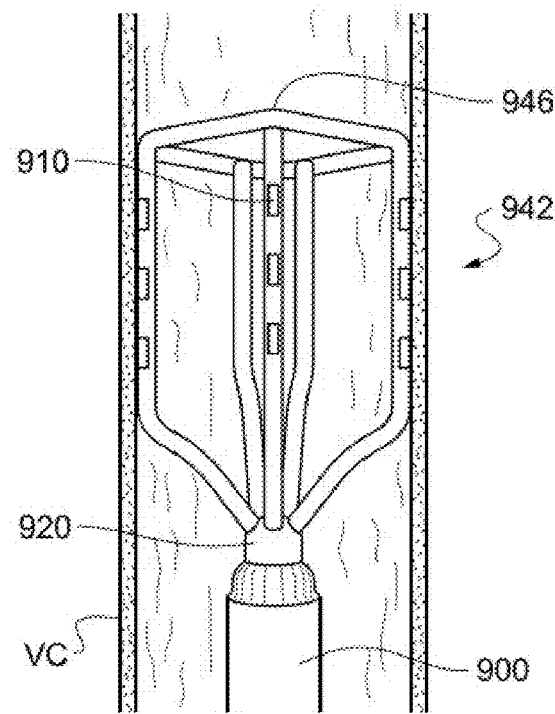
FIG. 9 shows an example of the catheter for phrenic nerve stimulation having an umbrella configuration.

FIG. 9 shows another example of a catheter 900 with expandable portion 942, wherein the expanded configuration is an umbrella configuration. The expandable portion 942 of the umbrella configuration may consist of one more flexible "ribs" (i.e., segments), where an endpoint of each rib is attached to an endpoint 920 on the expandable portion 942 of the stimulation catheter 900, and the other endpoint of the ribs are radially connected by a radial endpoint connector 946. In a straightened configuration, the segments may be put together longitudinally along the stimulation catheter, as the radial endpoint connector 946 may be contracted by the operator. When the stimulation catheter is in an expandable configuration, the radial endpoint connector 946 is in an expanded configuration, thereby being displaced outwards to the walls of the vein. In other words, the ribs of the umbrella are deployed along the walls of the vein. FIG. 9 shows the ribs expanding outwards from a longitudinal view. The displacement may be reversible and it may set the ribs at a fixed position between the straightened configuration and the maximal displacement allowed by the radial endpoint connector 946. One or more electrodes 910 may be arranged on each rib.

Figure 10:
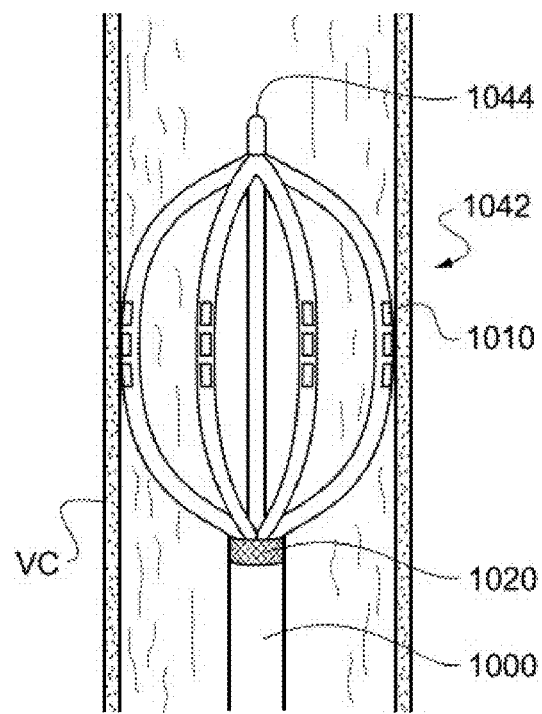
FIG. 10 shows an example of the catheter for phrenic nerve stimulation having a basket configuration.
Figure 11:
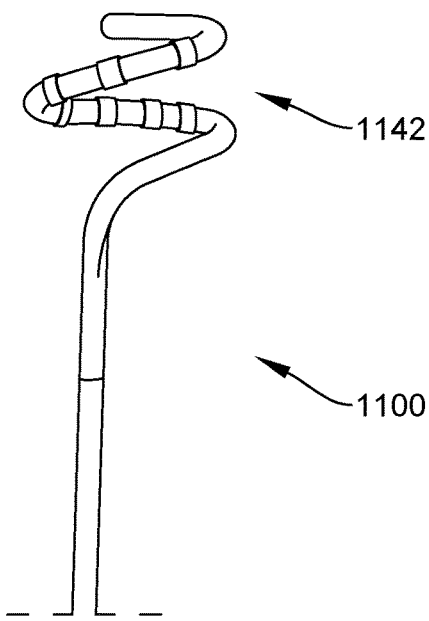
FIG. 11 shows an example of the catheter for phrenic nerve stimulation having an expandable portion.
Figure 12:
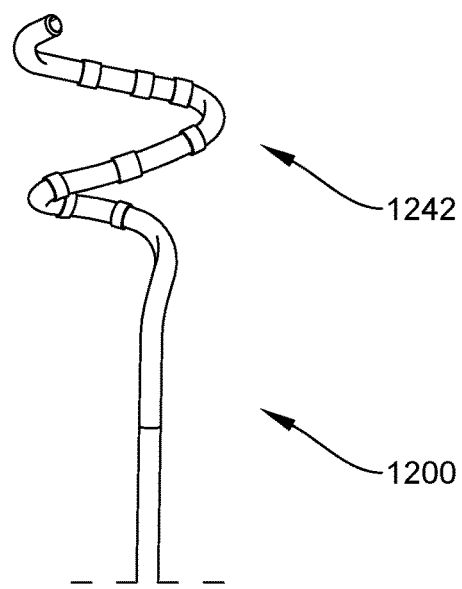
FIG. 12 shows an example of the catheter for phrenic nerve stimulation having an expandable portion.
Figure 13:
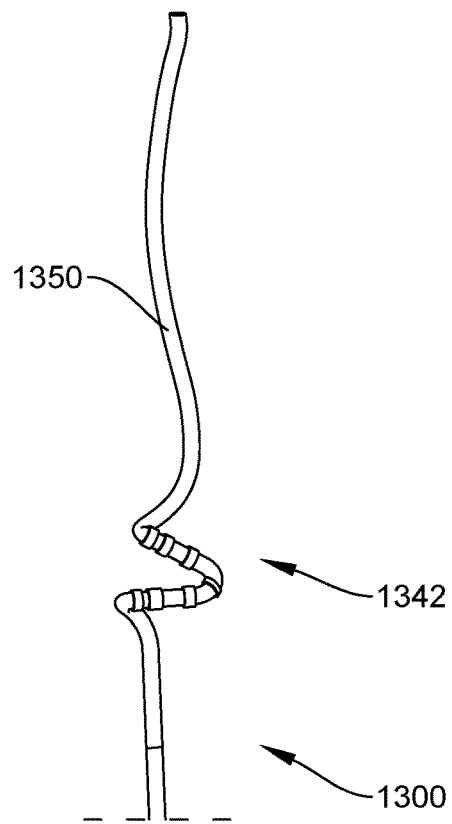
FIG. 13 shows an example of the catheter for phrenic nerve stimulation having an expandable portion and a non-expandable distal end.
Figure 14:
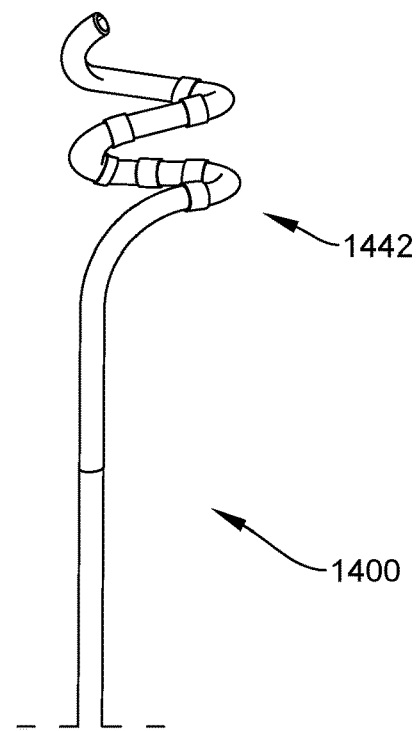
FIG. 14 shows an example of the catheter for phrenic nerve stimulation having an expandable portion.
Figure 15:
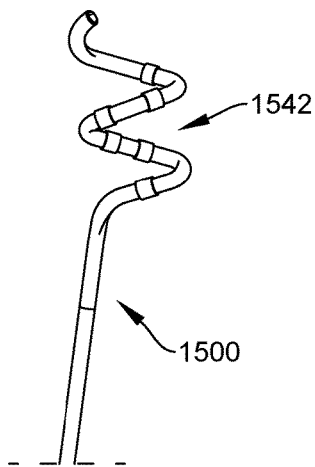
FIG. 15 shows an example of the catheter for phrenic nerve stimulation having an expandable portion.

FIG. 10 shows another example of a catheter 1000 with expandable portion 1042, wherein the expanded configuration is a basket configuration. The expandable portion 1042 of a basket configuration may consist of several "splines". Each spline is a segment comprising two endpoints. One endpoint of each spline is attached to the proximal end 1020 of the expandable portion 1042. The remaining endpoints of each corresponding spline is attached with each other via a mechanical attachment, forming a spline endpoint 1044. Each spline may be made of flexible material that allows the deployment from a straightened to an expandable configuration. In a straightened configuration, the splines are tensed along the longitudinal section of the expandable portion 1042, thereby forming a straight body extending along the endpoints 1020 and 1044 and parallel to the longitudinal axis of the catheter 1000. In the expandable configuration, the splines are displaced outwards, thereby creating a "basket" enclosing a volume.

FIG. 10 shows the splines being displaced circumferentially from the endpoints 1020 and 1044. This is just an example. For example, each spline may follow a piecewise linear path connecting endpoints 1020 and 1044. Each of the splines comprises a plurality of intravascular electrodes 1010. The basket configuration may comprise more than two splines, like four splines or eight splines or more. FIG. 10 shows intravascular electrodes 1010 located in the central section of the splines, and equally spaced between each other. The intravascular electrodes 1010 are located in an outward direction so as to be in contact with the walls of the vein.

The disclosed stimulation method and system were assessed in a 3D simulation.

The 3D simulation consisted in representing, in a finite element analysis software, a 3D model of the human body comprising a model of the thoracic area, which includes an anatomical model of the heart and the phrenic nerve, with associated electric resistance. The 3D model comprised a model of a catheter and an affixed extracorporeal patch. The 3D model was subject to settings representing the bipolar operation of the intravascular electrodes with the patch electrode. The electric field was simulated, and efficient stimulation of the phrenic nerve was assessed. The simulation comprised stimulating the phrenic nerve with a helicoidal catheter similar to the catheter described in FIG. 4 and the extracorporeal patch having a total area 168 $cm^2$, with a rectangular shape of length 20 cm and width 8 cm. Results of the simulation are compared with a mean reference response and an optimal reference response from the modelization of a quadripolar catheter widely used for phrenic nerve stimulation.

The simulation results yield an improvement with respect to the mean reference response and the optimal reference response of respectively 80% and 26%.

The disclosed stimulation method and system were further experimentally tested on a subject pig of 49 kg in weight.

Protocol:

Pork of 49KG, under general anesthesia, in dorsal decubitus position. Anesthesia is performed with Ketamine, Acepromazine, Diprivan and Sevoflurane. Care is taken to avoid all curare.

Steps:
A deflectable 6 French quadripolar electrophysiology catheter is positioned via the right femoral venous route in the superior vena cava.
A large plate-type electrocautery electrode patch is positioned in the back of the animal in the right paravertebral line.
Electrodes 1 and 4 of the catheter and the adhesive skin electrode patch are connected to an external pacemaker type temporary pacemaker. The stimulation can be done in bipolar mode at 12V×3 ms at a frequency of 60/min.
The quality of stimulation of the right phrenic nerve can be objectively assessed by performing a diaphragmatic electromyography of the right dome. A right diaphragmatic CMAP (Compound Motor Action Potential) is recorded using a pair of skin electrodes 15 cm apart positioned on the skin facing the right costal edge (modified DI lead). This recording is made by an ECG machine according to standard parameters, i.e., 25 mm/second and 10 mm/mV. The CMAP measurements are carried out on millimeter ECG paper.

The manipulation takes place in three phases.

Phase 1: comparison of the two stimulation modes, i.e., stimulation according to the prior art and according to the disclosure.

Under fluoroscopy, the catheter is positioned on twelve different sites at the level of the superior vena cava (SVC). Each position was evaluated by performing three fluoroscopy views: frontal view, right anterior oblique view 45° and left anterior oblique view 45°. The twelve different sites are distributed homogeneously in the SVC (cranial-caudal/anterior-posterior/lateral-median).

Without moving the catheter, on each site it is carried out successively:
Phrenic nerve stimulation according to the prior art, i.e., stimulation with the catheter in expanded bipolar mode, between electrodes 1 (anode) and 4 (cathode) of the catheter.
Bipolar stimulation between the distal electrode of the catheter (electrode 1 set as anode) and the dorsal skin electrode patch (set as cathode).
For each site, the quality of the phrenic capture can be assessed by measuring the amplitude of the diaphragmatic CMAP, measured in mm and collected in a spreadsheet.

Then, the catheter is moved to another site.

Phase 2: evaluation of the impact of contact of the electrode and the posterior wall of the SVC.

During bipolar stimulation between the distal electrode of the catheter and the dorsal skin electrode patch, the catheter is positioned successively:
Floating in the lumen of the vessel.
Resting on the anterior wall.
Resting on the posterior wall.
Four catheter positions at the height of the SVC are evaluated.

The obtained CMAP measurements are collated in a spreadsheet.

Phase 3: evaluation of the minimum size of the dorsal skin electrode patch.

The catheter is positioned in the SVC. Bipolar stimulation is performed between the distal electrode of the catheter and the dorsal skin electrode patch.

In this position, the stimulation is tested with decreasing sizes of the dorsal skin patch by cutting the skin electrode patch. Two centimeters in length and two centimeters in width are successively removed until capture of the phrenic nerve is incomplete, assessed by the amplitude of the CMAP. This manipulation can be carried out again while preserving the length of the adhesive electrode, but by cutting it only in its width.

It can be determined in this way the impact of size of the skin electrode patch on the results.

Results:

In the experimental testing, from the bipolar stimulation between the distal electrode of the catheter and the dorsal skin electrode patch an average CMAP along all the tested positions of 2.5 mV was obtained. In contrast, conventional stimulation with the catheter in expanded bipolar mode obtained an average CMAP of 1.8 mV.

There was an average CMAP improvement of up-to 40% by using bipolar stimulation between the distal electrode of the catheter and the dorsal skin electrode patch with respect to the average CMAP obtained by using conventional stimulation.

The operation in bipolar mode between the dorsal skin electrode patch and the intravascular electrodes can be performed in the same manner by inverting the polarity of the electrode of the catheter and the dorsal skin electrode patch. Inversion of the polarity did not modify the quality of the stimulation and/or amplitude of the obtained CMAP.

It is noted that increase in the area of the dorsal skin electrode patch appeared beneficial for the amplitude of the CMAP.

Bipolar stimulation with the catheter resting on any of the anterior and posterior walls of the SVC yielded particularly good results.

Several positions for the electrode patch were tested. Posterior para-vertebral right positions performed in the same way as the right latero-thoracic positions. On the other hand, anterior positions (i.e., on the subject's chest) showed decreased performance.

In a specific implementation, the distal portion of the catheter comprises a helical or spiral expandable portion configured to circumferentially fit the inner wall of the superior vena cava (VC), of the right brachiocephalic vein, and/or of the right subclavian vein, so as to remain in position during phrenic nerve stimulation.

The catheter may or may not further comprise a non-expandable distal end (or tip) distally located after the expandable portion. The distal end (if any) may for example be straight, and/or have a length higher than 1 cm, and/or lower than 12 cm, for example between 1.5 cm and 4 cm.

The expandable portion may have at most two coils in the expanded configuration. The expandable portion may have a diameter between 10 mm and 35 mm in the expanded configuration, i.e., an unconstrained expanded configuration.

Additionally, the catheter may comprise a lumen for introducing a retractable inner straightening member. The catheter may further comprise the inner straightening member inside the lumen. The inner straightening member may be a guidewire. The guidewire may be metallic, may present a diameter above 0.030" and/or below 0.040", for example equal to 0.032" or to 0.035", and/or may be made of a hydrophobic material.

According to the same implementation, the one or more intravascular electrodes may comprise a plurality of electrodes electrically connected together so as to form a single pole, or a plurality of individual electrodes electrically disconnected one from the other and operable altogether as a single pole.

Alternatively, the system may be configured for operating the plurality of electrodes so as to deliver simultaneously an electric pulse between each respective electrode of the plurality of electrodes and the extracorporeal electrode patch. The one or more intravascular electrodes may comprise for example between five and twenty electrodes, for example ten electrodes.

Figure 16:
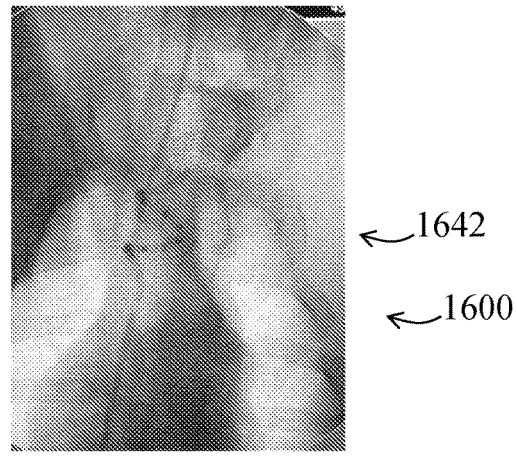
FIG. 16 shows an example of the catheter for phrenic nerve stimulation having an expandable portion.
Figure 17:
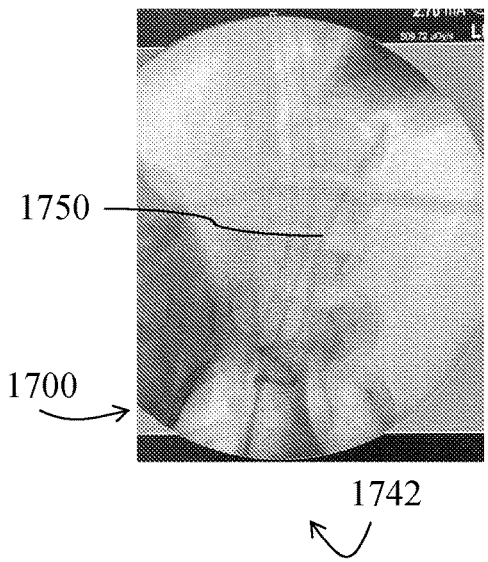
FIG. 17 shows an example of the catheter for phrenic nerve stimulation having an expandable portion and a non-expandable distal end.
Figure 18:
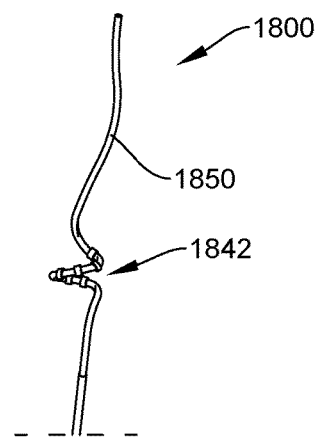
FIG. 18 shows an example of the catheter for phrenic nerve stimulation having an expandable portion and a non-expandable distal end.

FIG. 11 to FIG. 18 show examples of catheters 1100, 1200, 1300, 1400, 1500, 1600, 1700, 1800 according to such implementation and having an expandable portion 1142, 1242, 1342, 1442, 1542, 1642, 1742, 1842. As displayed in FIGS. 13, 17, and 18, a non-expandable distal end 1350, 1750, 1850 may be distally located after the expandable portion. FIG. 16 displays a catheter 1600 having an expandable portion 1642 with a diameter of 15 mm placed in the superior vena cava of a pig. FIG. 17 displays a catheter 1700, having an expandable portion 1742 with a diameter of 21 mm and a straight non-expandable distal portion 1750, placed in the superior vena cava of a pig. FIG. 18 displays a catheter 1800, having an expandable portion 1842 with a diameter of 21 mm and a straight non-expandable distal portion 1850.

Such an implementation of the system was experimentally tested on a subject pig of 45 kg in weight. The subject pig was placed under general anesthesia and in the dorsal decubitus position. Stimulation of the phrenic nerve was executed using ten electrodes of the catheter (anode) in bipolar mode with an extracorporeal electrode patch (cathode) positioned on the right dorsal side of the animal.

Material:
Hydrophobic stiff J-tip guidewire of 0.032"
8F introducer
Tested Prototypes:

TABLE 1

| # | Tube ø (F) | Braided tube length (cm) | Main tube hardness (Sh) | Interior tube hardness (Sh) | Distal part helix ø (mm) | Number of helix | Distal part shape | Electrode configuration |
|---|---|---|---|---|---|---|---|---|
| 1 | 7.5 | 120 | 40D | 72D | 21 | 1 | Single spire helix | Non isolated electrodes |
| 2 | 7.5 | 120 | 40D | 72D | 21 | 1 | Bigger helix increment | Non isolated electrodes |
| 3 | 7.5 | 120 | 40D | 72D | 21 | 1 | Helix with a straight tube at the distal extremity | Non isolated electrodes |
| 4 | 7.5 | 120 | 40D | 72D | 15 | 1 | Single spire helix | Non isolated electrodes |
| 5 | 7.5 | 120 | 40D | 72D | 15 | 1 | Single spire helix | Partially isolated electrodes |

Results:

TABLE 2

| Prototype # | Stimulation quality | Helix positioning by removing the J tip guidewire | Helix positioning by torque | Catheter extraction |
|---|---|---|---|---|
| 1 | 18/20 | 13/20 | 18/20 | 20/20 |
| 2 | 18/20 | 15/20 | 18/20 | 20/20 |
| 3 | 18/20 | 20/20 | 20/20 | 20/20 |
| 4 | 18/20 | 18/20 | 18/20 | 20/20 |
| 5 | 18/20 | 18/20 | 18/20 | 20/20 |

Prototype samples 1 to 5 mentioned in tables 1 and 2 correspond to the expandable portion samples displayed in FIG. 11 to FIG. 15 respectively. The results capture performance via a mark out of 20, 1/20 denoting minimal performance and 20/20 maximal performance. For all variations tested, the diaphragmatic stimulation was very good. Sample 3, which was provided with a straight non-expandable distal end, performed best mechanically. The positioning of the guide in the vena cava was facilitated by the fact that the non-expandable distal end was straight. It was also very easy to position, repull and reposition the coil in the vena cava even without the help of the guide. The coil remained horizontal and did not position itself diagonally, despite the fact that it had a 21 mm diameter (i.e., in an unconstrained expanded configuration).

The invention claimed is:

1. A method comprising performing phrenic nerve stimulation, the phrenic nerve stimulation including:
   providing a catheter including one or more intravascular electrodes each arranged on a distal portion of the catheter;
   providing an extracorporeal electrode patch having a conductive surface, the conductive surface being operable in a bipolar mode with the one or more intravascular electrodes;
   introducing the stimulation catheter in the superior vena cava of a human patient;
   positioning the distal portion of the catheter at a location in the superior vena cava, in the right brachiocephalic vein, and/or in the right subclavian vein;
   affixing the extracorporeal electrode patch to a human patient opposite to the distal portion relative to a phrenic nerve of the human patient, such that the conductive surface of the extracorporeal patch is located at least partly on a right half of a back of the patient and/or at least partly on a right side of an upper body of the patient, across the phrenic nerve from the location of the distal portion;
   operating the extracorporeal electrode patch in a bipolar mode with the one or more intravascular electrodes to perform phrenic nerve stimulation.

2. The method of claim 1, wherein the extracorporeal patch is positioned such that at least part of the conductive surface of the extracorporeal patch is at substantially a same height as the distal portion of the stimulation catheter, with respect to the patient's height.

3. The method of claim 2, wherein the extracorporeal patch is affixed such that the conductive surface of the extracorporeal patch is located below and substantially up to the base of the neck, below and substantially up to the right shoulder, or below and substantially up to the right armpit.

4. The method of claim 1, wherein the extracorporeal electrode patch is affixed such that the conductive surface of the extracorporeal patch is located at least partly to the back at the right paraspinal of the patient, facing the inner part of the right scapula, and the extracorporeal electrode patch goes up to the base of the neck.

5. The method of claim 1, wherein the extracorporeal electrode patch is affixed such that the conductive surface of the extracorporeal patch is located at least partly to the right latero-thoracic region of the patient.

6. The method of claim 1, wherein the extracorporeal electrode patch is affixed such that the conductive surface of the extracorporeal electrode patch extends along the back or right side of the patient, or such that the conductive surface of the extracorporeal electrode patch extends laterally along the back and the right side of the patient.

7. The method of claim 1, wherein the stimulation method further comprises monitoring a diaphragmatic response to the phrenic nerve stimulation.

8. The method of claim 1, the method comprising:
   introducing a cryoablation catheter inside a left atrium of a human patient; performing cryoablation; and
   while performing cryoablation, repeating the phrenic nerve stimulation.

9. The method of claim 8, wherein the method further comprises, when the diaphragmatic response decreases, pausing the cryoablation, and resuming the cryoablation afterwards.

* * * * *